(12) United States Patent
Segesser

(10) Patent No.: US 8,992,455 B2
(45) Date of Patent: Mar. 31, 2015

(54) METHODS, APPARATUSES AND SYSTEMS FOR CAVAL STENTING FOR VENOUS DRAINAGE

(75) Inventor: Ludwig Von Segesser, Lausanne (CH)

(73) Assignee: Coraflo Ltd., Lausanne (CH)

( * ) Notice: Subject to any disclaimer, the term of this patent is extended or adjusted under 35 U.S.C. 154(b) by 819 days.

(21) Appl. No.: 12/500,516

(22) Filed: Jul. 9, 2009

(65) Prior Publication Data

US 2010/0036307 A1    Feb. 11, 2010

Related U.S. Application Data

(60) Provisional application No. 61/079,348, filed on Jul. 9, 2008.

(51) Int. Cl.
| | |
|---|---|
| *A61M 5/00* | (2006.01) |
| *A61M 29/00* | (2006.01) |
| *A61M 37/00* | (2006.01) |
| *A61M 1/36* | (2006.01) |
| *A61B 17/34* | (2006.01) |
| *A61M 25/00* | (2006.01) |

(52) U.S. Cl.
CPC ............. *A61M 37/00* (2013.01); *A61M 1/3659* (2013.01); *A61B 17/3439* (2013.01); *A61M 25/007* (2013.01); *A61M 2205/0266* (2013.01)
USPC ............................................. 604/8; 606/192

(58) Field of Classification Search
USPC ............. 604/4.01, 5.09, 6.11, 6.16, 506–508; 606/191, 192, 194
See application file for complete search history.

(56) References Cited

U.S. PATENT DOCUMENTS

| | | | |
|---|---|---|---|
| 6,673,042 B1 * | 1/2004 | Samson et al. ................ | 604/104 |
| 2005/0038408 A1 | 2/2005 | Von Segesser | |
| 2005/0119597 A1 | 6/2005 | O'Mahony et al. | |

FOREIGN PATENT DOCUMENTS

| | | | |
|---|---|---|---|
| EP | 1839601 A1 | 10/2007 | |
| WO | 01/13983 A2 | 3/2001 | |
| WO | 01/37921 A1 | 5/2001 | |
| WO | 2005/002454 A1 | 1/2005 | |

OTHER PUBLICATIONS

Medical dictionary definition of "shaft" (2010).*
International Search Report, Application No. PCT/IB2009/006563, Date of Mailing: Feb. 18, 2010.
Written Opinion of ISA, Application No. PCT/IB2009/006563, Date of Mailing: Feb. 18, 2010.
Antonio F. Corno, Systemic venous drainage: can we help Newton?, *European Journal of Cardio-thoracic Surgery* 31 (2007); 1044-1051.
Matthias E.W. Kirsch, et al. "Kinetic assisted venous drainage for orthotopic heart transplantation in patients under mechanical circulatory support: a double-edged sword"; *European Journal of Cardiothoracic Surgery* 33, Mar. 2008; 418-423.
Hendrik T. Tevaearai, et al., "Venous Drainage with a Single Peripheral Bicaval Cannula for Less Invasive Atrial Septal Defect Repair"; *Ann Thorac Surg* 2001; 72; 1772-1773.

(Continued)

*Primary Examiner* — Melanie Hand
(74) *Attorney, Agent, or Firm* — Mintz Levin Cohn Ferris Glovsky and Popeo, P.C.

(57) ABSTRACT

A self expanding cannula with improved drainage properties based upon its greater length is provided, along with methods of using the cannula in cardiopulmonary bypass.

23 Claims, 22 Drawing Sheets

(56) References Cited

OTHER PUBLICATIONS

Xavier M. Mueller, et al., "Vacuum Assisted Venous Drainage Does Not Increase Trauma to Blood Cells"; *ASAIO Journal* 2001; 47; 651-654.
Ludwig K. von Segesser, (2006); "Peripheral cannulation for cardiopulminary bypass"; *Multimedia Manual of Cardiothoracic Surgery* doi:10.1510/mmcts. 2005.001610.
Ludwig K. von Segesser (1999); Cardiopulminary Support and Extracorporeal Membrane Oxygenation for Cardiac Assist; , *Ann Thorac Surg* 1999;68: 672-677.
David Jegger, et al., "Limitations using the vacuum-assist drainage technique during cardiopulminary bypass procedures" *J. Extra-Corpor Technol* 2003; 35: 207-211.
Mueller, et al., "Optimized venors return with a self-expanding cannula: from computational fluid dynamics to clinical application"; *Interactive Cardiovascular and Thoracic Surgery* 1 2002; 23-27.
Ludwig K. von Segesser; et al., The Smart Canula™: A New Tool for Remote Access Perfusion in Limited Access Cardiac Surgery:; *The Heart Surgery Forum* #2005: 8: E241-245.
Yi-ming Ni, et al., Optimization of venous return tubing diameter for cardiopulmonary bypass: *European Journal of Cardio-Thoracic Surgery* 20 (2001): 614-620.
Mueller, et al, "A New Expandable Venous Cannula for Minimal Access Heart Surgery"; *Ann Thorac Surg.* Oct. 2002; 74: S 1330-3.
Ludwig K. von Segesser, et al., "Routine use of self-expanding venous cannuls for cardiopulmonary bypass: Benefits and pitfalls in 100 consecutive cases", *European Journal of Cardio-thoracic Surgery* 34 (2008) 635-640.
Runge et al., Comparison of a Steady Flow Pump to a Preload Responsive Pulsatile Pump in Left Atrial-to-Aorta Bypass in Canines:; *Artificial Organs* Feb. 1991; 15(1):35-41.
Ludwig K. von Segesser, et al., "Routine Use of Intravascular Ultrasound for Endovascular Aneurysm Repair: Angiography is Not Necessary", *Eur J Vase Endovasc Surg* 23, Jun. 2002; 537-542.
Jegger, David; "Augmented Venous Return for Minimally Invasive Open Heart Surgery with Selective Caval Cannulation"; *European Journal of Cardio-thoracic Surgery*, 16:312-316 (1999).
Wenger, Robert K.; "Flow Dynamics of Peripheral Venous Catheters During Extracorporeal Membrane Oxygenation with a Centrifugal Pump"; *Journal of Thoracic Surgery*, 96:478-484 (1988).

* cited by examiner

Unstented Inferior Vena Cava

☐ Smart 43
● Standard

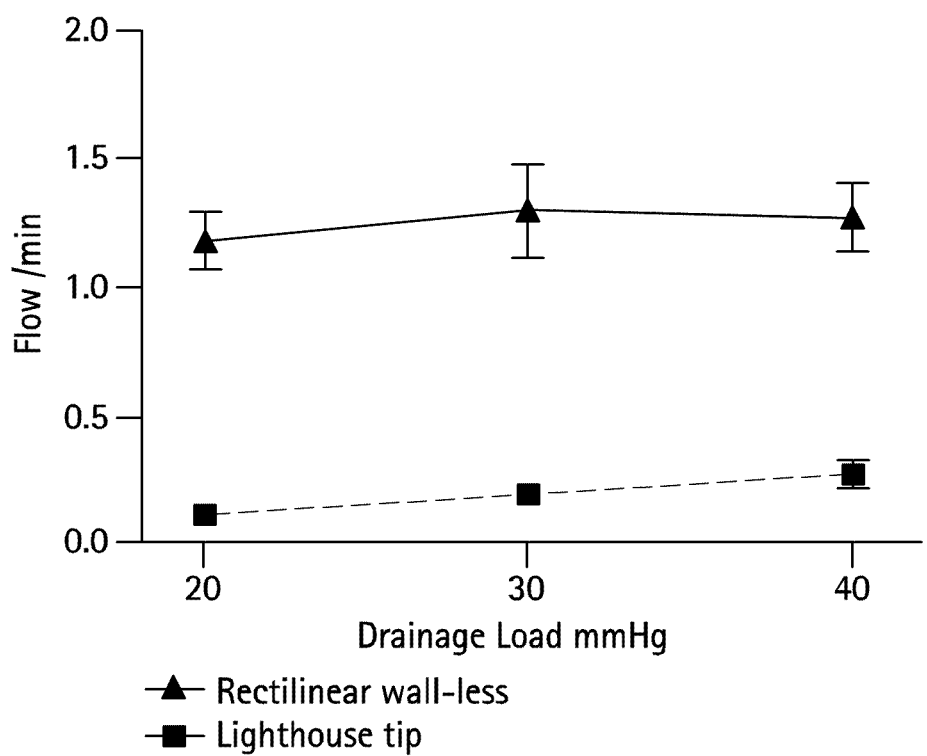

METHODS, APPARATUSES AND SYSTEMS FOR CAVAL STENTING FOR VENOUS DRAINAGE

CROSS-REFERENCE TO RELATED APPLICATIONS

This application claims the benefit of priority to U.S. Provisional Application No. 61/079,348, filed Jul. 9, 2008, and incorporates its disclosures herein by reference in its entirety.

FIELD OF THE DISCLOSURE

The application relates to methods, apparatuses and systems used in providing improved drainage during cardiopulmonary bypass (CPB), and more particularly, the use of longer-length as well as self-expanding cannulas to accomplish such improved drainage.

BACKGROUND

The venous vasculature is made from thin walled vessels which can hold a variable amount of blood. In the physiologic setting, venous pressure is low, but usually positive. Hence, the veins are distended up to some degree and the blood can flow back to the heart almost without resistance.

In open heart surgery the situation is different for a number of reasons. First, the entire systemic blood flow which is usually brought to the heart by several veins (inferior vena cava, superior vena cava, sinus venosis, thebesian veins, etc.) has to be drained towards the pump oxygenator through one single venous line and one or two venous cannulas. Moreover, for remote venous cannulation, the access vessel is relatively small, as compared to the central portion of the inferior vena cava, and therefore, unphysiological negative pressure has to be applied in order to suck the blood through a relatively narrow venous cannula. Even with central cannulation of the right atrium, only relatively short cannulas are used which drain the heart at the level of the right atrium and a part the inferior vena cava, typically at the level of the liver. The remainder of the venous system remains unsupported and collapses in regular fashion during the extracorporeal circulation. This phenomenon is well known and described by the term "atrial" chatter.

With bicaval central cannulation, the situation is most often worse, because the caval veins are supported only for a few centimeters and the remainder collapses as a function of the negative pressure applied. Major volume loss at the time of passing from partial cardio-pulmonary bypass (unsnared venae cavae) to total cardio-pulmonary bypass (snared venae cavae) is a well known problem and sometimes difficult to solve. Often, venous return must be augmented for open heart surgery with cannulation. (Jeger et al. European Journal of Cardio-thoracic Surgery 16:312-316 (1999), incorporated herein, in its entirety.)

Accordingly, inadequate venous drainage during cardiopulmonary bypass has many drawbacks (Eur. J. Cardiothorac. Surg., June 2007; 31: 1044-1051). As a matter of fact, the amount of venous blood drained from the patient not only determines the pump flow that can be achieved during cardiopulmonary bypass (CPB) and is crucial for adequate end organ perfusion, but also defines the amount of blood that stays in the patients cardio-vascular system during the procedure. Hence, in addition to superior perfusion, improved venous drainage has also the potential to simplify the surgical procedure (Eur. J. Cardiothorac. Surg., March 2008; 33: 418-423). Considering the on-going trend towards minimal access procedures, the latter aspect is of prime interest (Ann Thorac Surg 2001; 72: 1772-1773).

There are numerous factors that can influence the quality of venous drainage during CPB including venous cannula design, venous cannula positioning, pump set-up etc. (Cardiothorac. Surg., June 2007; 31: 1044-1051). For remote venous cannulation (i.e. trans-femoral or trans-jugular) long thin walled, rectilinear venous cannulas are traditionally used in conjunction with a centrifugal pump or vacuum for augmentation of flow (Ann Thorac Surg 2001; 72: 1772-1773; ASAIO J 2001; 47: 651-654). In this setting the multi-orifice cannula tip is usually positioned in the right atrium and the entire blood flow has to travel through the long and relatively narrow cannula lumen, which is essentially a function of the access vessel diameter. Unfortunately, only about 90% of the theoretical target pump-flow can be achieved with this technique (J Extra-Corpor Technol 2003; 35: 207; Ann Thorac Surg 68: 672-677).

Throughout this description, including the foregoing description of related art, any and all publicly available documents described herein, including any and all U.S. patents, are specifically incorporated by reference herein in their entirety. The foregoing description of related art is not intended in any way as an admission that any of the documents described therein, including pending United States patent applications, are prior art to embodiments of the present disclosure. Moreover, the description herein of any disadvantages associated with the described products, methods, and/or apparatus, is not intended to limit the disclosed embodiments. Indeed, embodiments of the present disclosure may include certain features of the described products, methods, and/or apparatus without suffering from their described disadvantages.

SUMMARY

According to some embodiments, methods are provided for vascular draining comprising: providing a venous cannula having a length of between 30 cm and 70 cm; positioning the cannula in a blood vessel; and applying a driving pressure of between about less than 15 to about 40 mmHg or more.

In some embodiments, the blood vessel is a vein.

In some embodiments, the method prevents venous collapse.

In some embodiments, the vascular drainage is performed during drainage for cardio-pulmonary bypass.

In some embodiments, the cannula is provided in a trans-jugular or trans-subclavian fashion.

In some embodiments, the cannula is provided in any one of: a trans-femoral, trans-iliac fashion, transjugular, and/or trans-subclavian.

In some embodiments, multiple cannulas are provided via any one or more of: trans jugular, trans-subclavian, and/or via the groin (trans-femoral or trans-iliac).

In some embodiments, the cannula is provided through the right atrium into the inferior vena cava, which reaches beyond the liver to the iliac or femoral vein. In some embodiments, the trans-femoral cannulation is performed by passing the cannula through the right atrium into the superior vena cava. In other embodiments, the cannula passes the subclavian vein. In other embodiments, the cannula enters the jugular vein.

In some embodiments, the trans-jugular or trans-subclavian cannulation are performed by passing the cannula through the superior vena cava and the right atrium into the inferior vena cava. Optionally, the cannula passes the iliac vein. Optionally, the cannula enters the femoral vein.

In some embodiments, multiple cannulas are provided, wherein at least one of the cannulas are provided through the right atrium into the superior and the inferior vena cava, and/or directly into both caval veins.

In some embodiments, the cannula is a self-expanding cannula, and/or includes an open wall design.

In other embodiments, the cannula is a rectilinear cannula with multiple side holes.

In some embodiments, use of the cannula results in drainage of between about 4 and 6 liters/min.

In some embodiments, use of the cannula results in drainage of between about 1 ml/min to more than 6 liters/min.

In some embodiments, drainage is enhanced via the use of a diabolo-shape of the cannula (e.g., venturi mechanism).

According to some embodiments, systems are provided for vascular draining comprising: a venous cannula having a length of between 30 cm and 70 cm; positioning means for positioning the cannula in a blood vessel; and pressurizing means for applying a driving pressure of between about less than 15 (e.g., 1-5 mmHg) to about 40 mmHg or more.

In more specific embodiments, the positioning means comprises a device selected from the group consisting of an obturator, a catheter, a mandrel, a sheath and a guidewire. In other specific embodiments, the pressuring means comprises a device selected from the group consisting of a centrifugal pump and a vacuum.

According to some embodiments, cannulas are provided having a length between 30 and 70 cm, comprising orifices and intravascular surfaces, wherein the orifices are larger than 5% of the intravascular surface.

In some embodiments, the cannula is a wall-less cannula. In other embodiments, the cannula has multiple orifices.

In some embodiments, the cannula is self-expanding. In other embodiments, the cannula is rectilinear in shape. In other embodiments, the cannula is comprised of torqued blades

BRIEF DESCRIPTION OF THE FIGURES

FIG. 23 is a line graph showing the improved flow of wall-less rectilinear cannulas over lighthouse tipped rectilinear cannulas at various drainage load pressures.

DETAILED DESCRIPTION

Figure 1A:
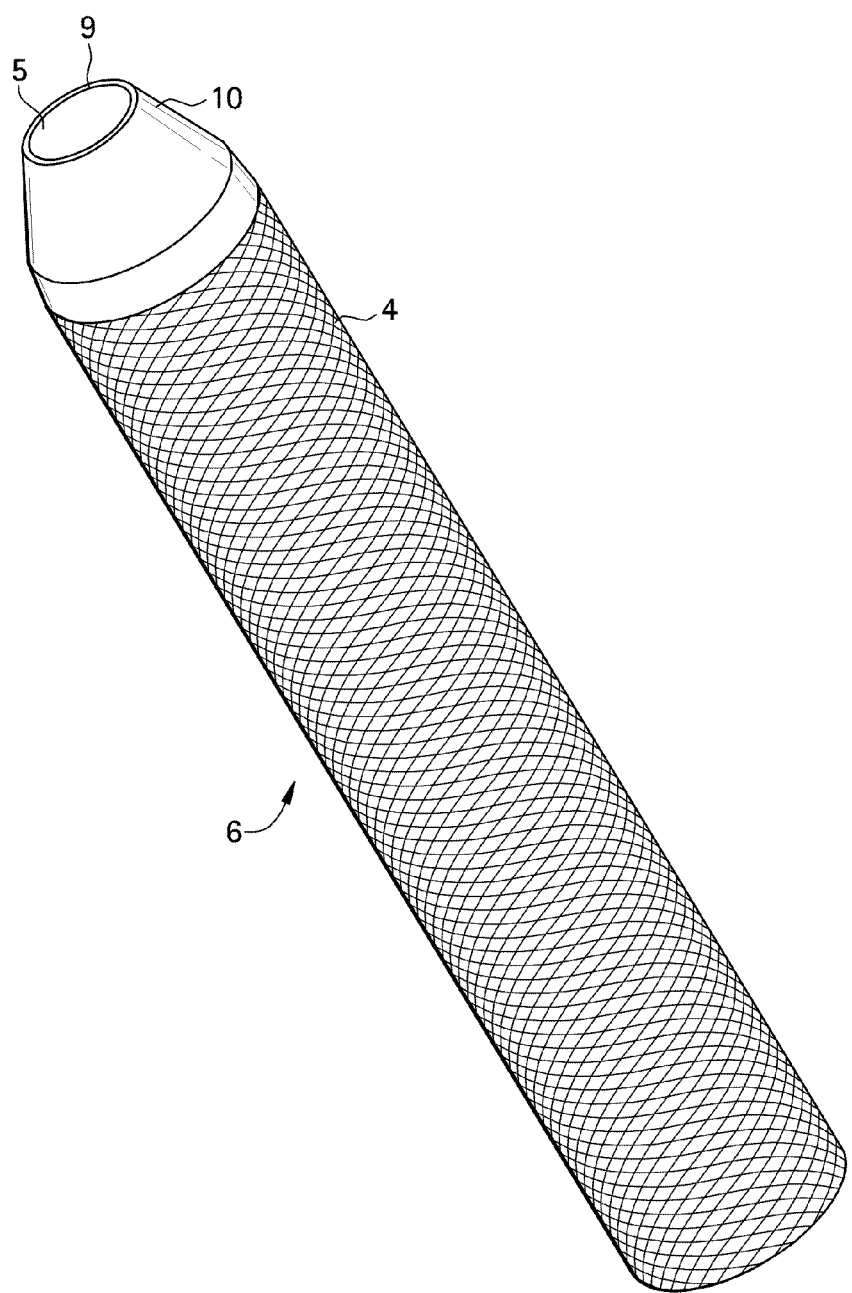
FIG. 1A illustrates a cannula according to one embodiment in its normal profile conformation. Cannulas according to this embodiment can be used, for example, in open heart and open chest surgical procedures.
Figure 1B:
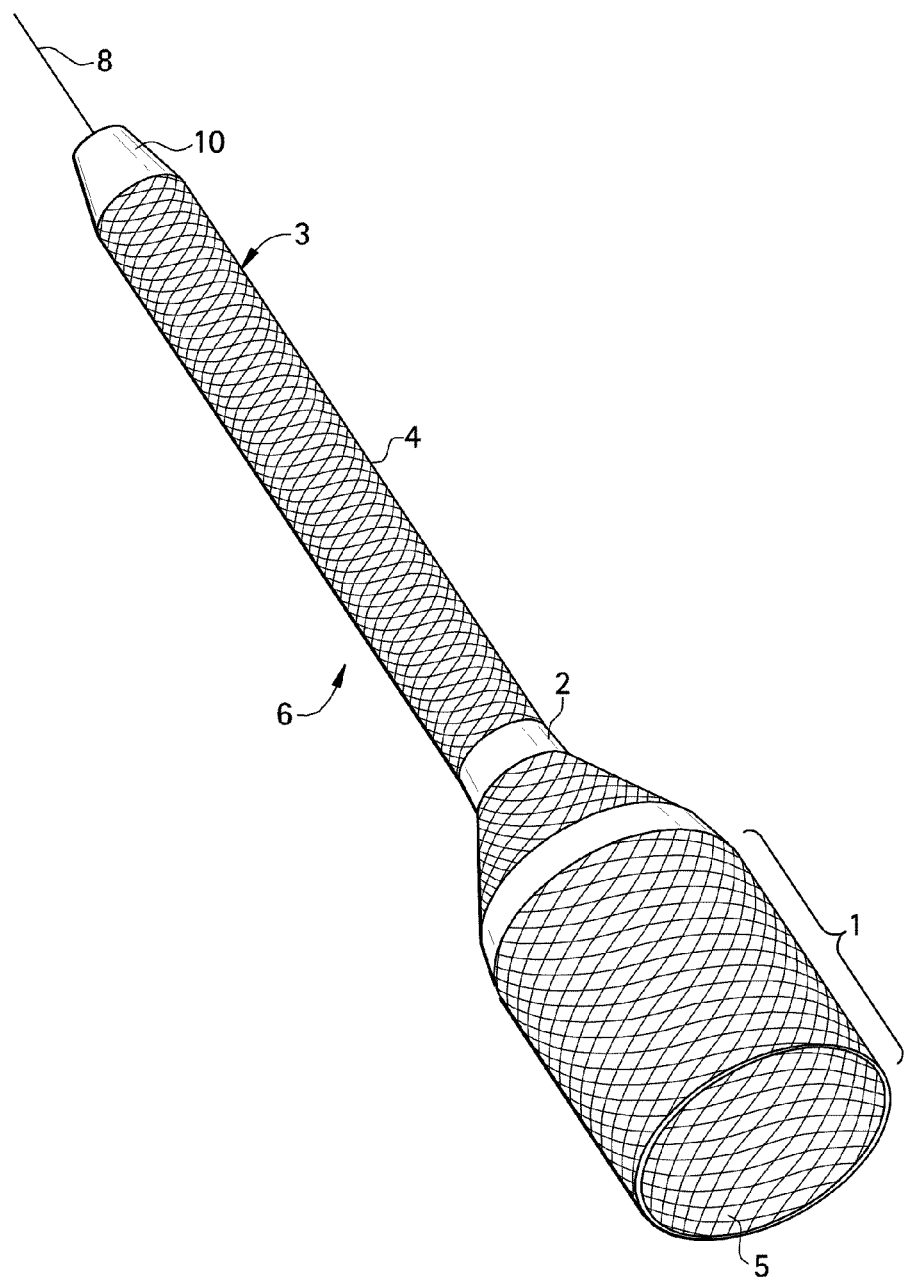
FIG. 1B illustrates a cannula according to one embodiment in its low profile conformation.

Accordingly, some embodiments of the subject disclosure are directed to methods, apparatuses and systems for caval stenting for venous drainage, particularly as may be applied during cardiopulmonary bypass.

According to some embodiments, methods are provided for vascular draining comprising: providing a venous cannula having a length of between 30 cm and 70 cm; positioning the cannula in a blood vessel; and applying a driving pressure of between about less than 15 to about 40 mmHg or more.

Thus, according to some embodiments, the driving pressure may be from about 5 mmHg to 60 mmHg, from about 10 mmHg to 50 mmHg, from about 15 mmHg to 40 mmHg, from about 20 mmHg to 40 mmHg, from about 25 mmHg to 40 mmHg, from about 30 mmHg to 40 mmHg, from about 35 mmHg to 40 mmHg, from about 15 mmHg to 35 mmHg, from about 15 mmHg to 30 mmHg, from about 15 mmHg to 25 mmHg, or from about 15 mmHg to 20 mmHg.

According to some embodiments, objectives may include assessing the benefit of temporary caval stenting for remote venous drainage during cardiopulmonary bypass (CPB). For example, in some embodiments, such objectives were realized in bovine experiments (e.g., 65±6 kg) by the means of, for example, self-expanding (e.g., 18F for insertion, 36F in situ) venous cannulas (e.g., Smartcanula LLC, Lausanne, Switzerland) with various lengths: e.g.: 43 cm, 53 cm, and 63 cm versus a standard 28F wire (for example) armed cannula in trans-jugular fashion. Accordingly, maximal blood flows were assessed for 20, 25 and 30 mmHg of driving pressure with a motorized table height adjustment system.

In addition, in some embodiments, the inferior caval diameters (just above its bifurcation) were measured in real time with intra-vascular ultrasound (IVUS). The results of such experiments, venous drainage (flow in l/min) at 20 mmHg, 25 mmHg, and 30 mmHg drainage load was 3.5±0.5, 3.7±0.7, and 4.0±0.6 for the 28F standard versus 4.1±0.7, 4.0±1.3, and 3.9±1.1 for the 36F smart 43 cm, versus 5.0±0.7, 5.3±1.3, and 5.4±1.4 for the 36F smart 53 cm, versus 5.2±0.5*, 5.6±1.1*, and 5.8±1.0* for the 36F smart 63 cm. The inferior vena caval diameters at 30 mmHg were 13.5±4.8 mm for 28F standard, 11.1±3.6 36F smart 43 cm, 11.3±3.2 for 36F 53 cm, and 17.0±0.1* for 36F 63 cm (*=p<0.05 for 28F standard versus 36F smart 63 cm long). Thus, according to some embodiments, the 43 cm self-expanding 36F Smartcanula® outperformed the 28F standard wire armed cannula at low drainage pressures and without augmentation. Moreover, according to some embodiments, temporary caval stenting with long self-expanding venous cannulas provided even better drainage (+51%).

In some embodiments, a method is presented which includes one or more of the following: use of longer venous cannulas for central or peripheral cannulation: support of the venous luminal width (temporary caval stenting) prevents collapsing and allows for better drainage; temporary caval stenting to support a major part (e.g., >20%) up to all of the caval axis and even some branches (like iliac veins, femoral veins, jugular veins); the open wall concept of the high flow cannula (coverage only at the level of insertion for sealing the cannulation site) allowing for drainage over the majority of the cannula length, because, the blood can enter the cannula lumen through the uncovered grid wherever it is available. The venous wall (supported) stent temporarily provides the seal, the cannula merely keeps it open; and a self-expanding version improves the drainage even further because the flow depends of the diameter by power four.

In addition to suggested braids or grids, there are other possibilities to prevent the veins from collapsing like ribs, wings, vanes, spirals, springs over the entire or part of the cannula length, which allow the blood to enter the cannula lumen directly and not only through a few discrete holes, for example.

In some embodiments, there may be an additional effect with a self-expanding version.

In some embodiments, longer cannulas of the invention provide better drainage than traditional cannulas (e.g., shorter, walled rectilinear cannulas). Prior art cannulas provide worse drainage when they are longer (i.e., resistance increases in linear fashion with length). In fact, in some embodiments of the cannulas of the invention, a venturi mechanism appears where the cannula leaves the vessel (i.e. narrowest place in the blood path) whereas just before, the cannula cage is wider, and thus improves flow (drainage). The cannula can also be made up of torqued blades which allows the cannula to be substantially wall-less.

Some embodiments also present methods of using a long venous cannula having an open wall and a fixed geometry with a narrow section at the cannulation site mimicking an injection nozzle in a open wall cage (before the cannula exits the vessel or the right atrium). Such embodiments have a similar flow enhancing effect.

In some embodiments, there is provided methods of temporary caval stenting by peripheral and central single, as well as dual cannulation.

Thus, some embodiments of the present disclosure are directed to the use of longer self-expanding cannulas inserted from the periphery (jugular or subclavian vein and femoral vein) to provide better drainage. In some embodiments, long cannulas are used not only for remote (femoral) cannulation, but also for routine central (right atrial) applications, in order to support the entire inferior vena cava.

Some embodiments include:

longer venous cannulas for central or peripheral cannulation temporarily stenting a major part (greater than, for example, 30%) or all of the caval axis;

drainage of substantially the entire intravascular part of the cannula;

an open wall concept of a high-flow cannula (i.e., coverage only at the level of insertion);

utilization of, for example, ribs, vanes, spirals, and/or the like, over (according to some embodiments) almost the entire or part of the cannula length of the cannula; in some embodiments, the entry site seals for the avoidance of air intake; such features may allow the blood to join the cannula lumen directly and not only through a few openings/holes; and self-expanding cannula providing improved drainage even further.

Figure 24:
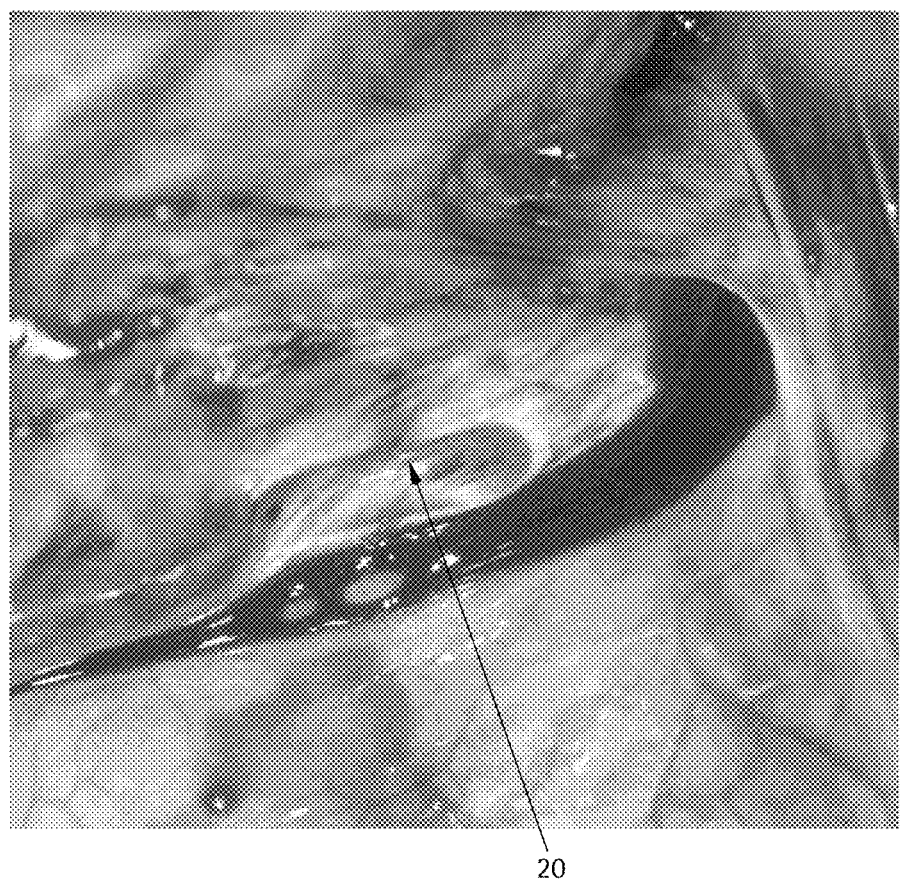
FIG. 24 shows a traditional cannula (20) sucking the wall of the vena cava into its orifices.

According to some embodiments of the present disclosure, increased flow, and moreover in some embodiments, full flow can be achieved without augmentation of venous drainage utilizing, for example a Smart Canula® (Smartcanula LLC, Lausanne, Switzerland), which is based on the "collapsed insertion and expansion in situ" principle (Interactive Cardio-Vascular and Thoracic Surgery 2002; 1: 23-27; The Heart Surgery Forum 2005; 8: E241-245; Herz-, Thorax-, Gefässchirurgie 2007; 21: 1-7; Eur J Cardio-thorac Surg 2001; 20: 614-620). With its self-expanding open wall design, the vein itself providing the seal, the smart cannula device may act also as a spacer preventing the vein from collapsing, and therefore, allow most or substantially all collateral blood (and preferably all) to be drained directly towards a pump oxygenator. An example of venous collapse is shown in FIG. 24. FIG. 24 shows a traditional cannula (20) sucking the wall of the vena cava into its orifices, stopping drainage and causing atrial chatter.

According to other embodiments of the present disclosure increased flow, and moreover in some embodiments, full flow can be achieved without augmentation of venous drainage utilizing, for example a long central rectilinear cannula with multiple holes.

Cannulas

The cannulas for use in the present methods are "long" or "longer" cannulas, which refers to cannulas having a length of about 30 cm to about 70 cm. This includes, but is not limited to, cannulas having a length of about 30 cm, about 32 cm, about 33 cm, about 34 cm, about 35 cm, about 36 cm, about 38 cm, about 40 cm, about 42 cm, about 43 cm, about 45 cm, about 47 cm, about 48 cm, about 50 cm, about 53 cm, about 55 cm, about 57 cm, about 58 cm, about 60 cm, about 63 cm, about 65 cm, about 67 cm, about 68 cm, about 70 cm, or about 75 cm. In some embodiments, the cannulas have a length of between about 35 cm to about 45 cm, between about 40 cm to about 50 cm, between about 45 cm to about 50 cm, between about 40 cm to about 45 cm, between about 30 cm to about 45 cm, between about 40 cm to about 55 cm, between about 45 cm to about 65 cm, between about 50 cm to about 65 cm, or between about 40 cm to about 65 cm. One of ordinary skill in the art would appreciate that children or neonatal patients require shorter lengths for stenting the caval veins. Thus, lengths will be proportionally shorter for cannulas used for patients that are children, infants or neonates.

In some embodiments, the cannulas are wall-less cannulas based on any type of spacer keeping the veins open and allowing for direct inflow. In some embodiments, the cannulas lack a rigid wall. In some embodiments, the cannulas are self-expanding or may be expandable by a mechanism.

The cannulas may take on any shape, such as, for example, tube or tubular or rectilinear. The shapes of the cannulas of the disclosure include circular, rectangular, oval, hexagonal, octagonal, and the like. For example, with central cannulation, where size is less of an issue, rectilinear longer "wall-less" cannulas may be used (e.g. temporary stents). Such cannulas should provide superior flow as compared to shorter designs with a few holes. In other embodiments, long central rectilinear cannula with multiple holes are used.

According to some embodiments, the cannulas may be branched cannulas, such as cannulas having a Y-shape from the beginning or may be assembled in several steps in order to stent temporarily not only the caval veins (or other vessels) but potentially some branches.

According to some embodiments, the cannulas are self expanding cannulas. According to some embodiments, the cannulas to be used in the present methods allow for collapsed cannula insertion, and self-expansion within a vein of the body.

According to some embodiments, the cannulas for use in the present methods may be described as a spring with a mesh configuration allowing for lateral inflow from collaterals. The cannula's proximal part may be watertight to avoid blood leaking outside of the body and at the introduction site, as well as to allow for connection to a standard venous line. For example, the selected cannula length may be 35 cm and its expanded outer diameter accounts for 12 mm (wall thickness: 1 mm). For insertion, a semi-rigid obturator (4 mm in diameter) may be placed centrally, within in the lumen of the cannula. The cannula is then stretched over the obturator and collapsed. The obturator as well as the tip of the cannula may have a central lumen in order to allow the cannula to slide over the guidewire (typically 0.034 inches in diameter). Once in place, the obturator is removed, allowing the inherent spring force to expand the cannula within the vein. For cannula removal, simple traction allows for progressive reduction of the cannula diameter, whereas cannula repositioning requires reinsertion of the obturator.

According to some embodiments, the Smartcanula® may be used in the methods of the present invention. Cannulas suitable for use in the present methods are disclosed in PCT publication nos. WO 2001/052753, to von Segesser, and WO 2005/002454, to von Segesser, both entitled, "High Performance Cannulas", the complete disclosures of which are herein incorporated by reference.

In preferred embodiments, the cannulas are used for central venous cannulation of adults. Preferably cannulas used for central venous cannulation for adults have a circumference between about 30 and about 36F at the access orifice. Preferably cannulas used for central venous cannulation for adults have an intravascular circumference of between about 30 and about 36F. Preferably, the intravascular portion of the cannula is rectilinear. Preferably cannulas used for central venous cannulation for adults have an intravascular length between about 33 and about 53 cm. The intravascular length of the cannula is dependent upon the body size of the patient the cannula is being used for. Preferably cannulas used for central venous cannulation for adults have a distance of between about 25 and about 45 cm between the most proximal and most distal orifice. Preferably cannulas used for central venous cannulation for adults have a total orifice surface of from about 27 to about 50 $cm^2$.

In other preferred embodiments, the cannulas are used for femoral venous cannulation of adults. Preferably cannulas used for femoral venous cannulation for adults have a circumference between about 21 and about 27F at the access orifice. Preferably cannulas used for femoral venous cannulation for adults have an intravascular circumference of between about 21 and about 27F. Preferably, the intravascular portion of the cannula is rectilinear. Preferably cannulas used for femoral venous cannulation for adults have an intravascular length between about 43 and about 73 cm. The intravascular length of the cannula is dependent upon the body size of the patient the cannula is being used for. Preferably cannulas used for femoral venous cannulation for adults have a distance of between about 34 and about 64 cm between the most proximal and most distal orifice. Preferably cannulas used for femoral venous cannulation for adults have a total orifice surface of from about 38 to about 70 cm$^2$.

In other preferred embodiments, the cannulas are used for subclavian/jugular venous cannulation of adults. Preferably cannulas used for subclavian/jugular venous cannulation for adults have a circumference between about 21 and about 27F at the access orifice. Preferably cannulas used for subclavian/jugular venous cannulation for adults have an intravascular circumference of between about 21 and about 27F. Preferably, the intravascular portion of the cannula is rectilinear. Preferably cannulas used for subclavian/jugular venous cannulation for adults have an intravascular length between about 43 and about 73 cm. The intravascular length of the cannula is dependent upon the body size of the patient the cannula is being used for. Preferably cannulas used for subclavian/jugular venous cannulation for adults have a distance of between about 34 and about 64 cm between the most proximal and most distal orifice. Preferably cannulas used for subclavian/jugular venous cannulation for adults have a total orifice surface of from about 38 to about 70 cm$^2$.

According to some embodiments, the cannulas may be coated with bio-compatibility/thromboresistance substance. The thromboresistance substance used may be any substance used as a non-thrombogenic coating for medical devices known in the art. For example, heparin may be used as a non-thrombogenic surface coating. According to some embodiments, the cannulas are heparin surface coated. According to some embodiments, the cannulas may be surface coated with a heparin containing polymer or composition. Such cannulas may be useful with long term perfusions or were less anticoagulants are used. This includes procedures requiring the use of a cannula for more than 12 hours (e.g., more than 24 hours, more than 3 days, more than 7 days, more than 14 days, more than 21 days) such as extracorporeal membrane oxygenation (ECMO).

According to some embodiments, the cannula may be adapted for insertion at a point of insertion. The cannula includes a cannula body having a proximal end, a distal end, and a lumen extending between the proximal and distal ends. The lumen has a diameter and the cannula body includes a plurality of flexible filaments that allow the diameter of the lumen to be varied. The distal end optionally further comprises a tip, which can be removable or eccentrically located. The cannula also includes at least one mechanism that, upon actuation, serves to alter the conformation of the cannula between a normal profile conformation and a low profile conformation. For example, the mechanism is selected from a mandrel, an electric motor, a change in pressurization, a wrapping string, a balloon and a sheath. When the cannula is in use, the normal profile conformation is characterized by the cannula having a lumen diameter at the point of insertion, which is smaller than the lumen diameter both proximal and distal to the point of insertion. The lumen diameter distal to the point of insertion is expandable up to the diameter of a surrounding vessel or up to the maximum lumen diameter.

The low profile conformation is characterized by the cannula having a lumen diameter at the point of insertion that is greater than the lumen diameter distal to the point of insertion.

The plurality of flexible filaments may include one or more materials selected from metals, shape-memory metals, alloys, plastics, textile fibers, synthetic fibers, and/or combinations thereof. For example, the metal can be stainless steel. Moreover, the plurality of flexible filaments can have a shape selected from round, oval, flattened, triangular, rectangular and combinations thereof. In one embodiment, the plurality of flexible filaments are textile fibers.

Those skilled in the art will recognize that the plurality of flexible filaments can be braided together, knitted together or interwoven. Alternatively, the plurality of flexible filaments are interlaced.

The cannula may be designed to be inserted into hollow organ, which can be selected from, for example, a vein, an artery, a urethra, a ureter, an intestine, an esophagus, a trachea, a bronchial tube, a pleural space, and/or a peritoneum.

According to some embodiments, when the cannula is in its normal profile conformation when in use, the lumen diameter distal to the point of insertion varies in relation to the diameter of the surrounding vessel. Further, the cannula is in its normal profile conformation when in use, the portion of the cannula distal to the point of insertion supports an inner surface of the surrounding vessel.

According to some embodiments, the plurality of flexible filaments may be elastic and/or plastic in nature. The cannula may be coated with a watertight coating, which can be a plastic, such as, for example, silicone. The cannula tip may be potted using a material such as a photoactivated epoxy. The cannula may further include a connecting sleeve to couple the cannula to a device.

In a preferred embodiment, the cannula has a wall-less design. In some aspects of this embodiment, the caval vein is kept open by the temporary stent generated by the wall-less end of the cannula. Less resistance is generated in a longer cannula with multiple orifices provided they stay open. In a wall-less cannula drainage is possible all over the outer circumference of the cannula. That is the reason for the concept of the wall-less design where the blood can enter the lumen of the cannula at any place. In other preferred embodiments, isolated orifices are positioned so that the vessel wall does not interfere with flow into the cannula. In more preferred embodiments, the orifices in the wall of the cannula have a total surface of one or more magnitudes larger than the cross sectional area of the cannula.

In another preferred embodiment, the cannulas of the disclosure have orifices areas larger than 5% of the intravascular surface. In another preferred embodiment, the cannulas of the disclosure have orifices areas larger than 6% of the intravascular surface. In another preferred embodiment, the cannulas of the disclosure have orifices areas larger than 7% of the intravascular surface. In another preferred embodiment, the cannulas of the disclosure have orifices areas larger than 8% of the intravascular surface. In another preferred embodiment, the cannulas of the disclosure have orifices areas larger than 9% of the intravascular surface. In another preferred embodiment, the cannulas of the disclosure have orifices areas larger than 10% of the intravascular surface. In another preferred embodiment, the cannulas of the disclosure have orifices areas larger than 25% of the intravascular surface. In another preferred embodiment, the cannulas of the disclosure have orifices areas larger than 50% of the intravascular surface. In another preferred embodiment, the cannulas of the disclosure have orifices areas larger than 75% of the intravascular surface. In another preferred embodiment, the cannulas of the disclosure have orifices areas larger than 85% of the intravascular surface. In another preferred embodiment, the cannulas of the disclosure have orifices areas larger than 90% of the intravascular surface. In another preferred embodiment, the cannulas of the disclosure have orifices areas larger than 95% of the intravascular surface. In another preferred embodiment, the cannulas of the disclosure have orifices areas larger than 98% of the intravascular surface. In another preferred embodiment, the cannulas of the disclosure have orifices areas larger than 99% of the intravascular surface.

The flow rate of fluid through the cannulas may be less than about 150 mL/min. In some of the cannulas, the flow rate of fluid through the cannula is between about 1 mL/min and about 10 L/min.

Methods of using the cannula in medical contexts may include placing the cannula in its low profile conformation, inserting the cannula into a hollow organ of a patient at a point of insertion, and returning the cannula to its normal profile conformation. In the normal profile conformation, the self expanding cannula expands distal to the point of insertion up to the diameter of the hollow organ or up to the maximum diameter of the lumen.

For example, when the cannula is in the normal profile conformation, the diameter of the cannula distal to the point of insertion varies in relation to the diameter of the hollow organ. Inserting the cannula into the hollow organ of the patient can include inserting the cannula into a location selected from the peritoneum, the trachea, the chest, the cardiovascular system, the kidneys, and the urinary system. For example, the hollow organ can be selected from a vein, an artery, a urethra, a ureter, an intestine, an esophagus, a trachea, a bronchial tube, a pleural space, and a peritoneum. In one specific embodiment, the cannula is inserted into the trachea, and the cannula can be inserted transorally, transnasally, or through a tracheotomy.

When the cannula is used during cardiac surgery, the cannula may have a flow rate of fluid through the cannula of between about 100 mL/min and 6 L/min. When used during dialysis or hemofiltration, the cannula may have a flow rate of fluid through the cannula between about 100 mL/min and 500 mL/min. When used for the intravenous delivery of fluids, the cannula may have a flow rate between about 1 mL/min and about 10 mL/min.

Dual lumen cannulas include a first cannula body having a proximal end, a distal end, and a lumen extending between the proximal and distal ends, and a second cannula body having a proximal end, a distal end, and a lumen extending between the proximal and distal ends, the lumen of the first and second cannula bodies having a diameter. The first and second cannula bodies each include a plurality of flexible filaments that allow the diameter of the first and second lumen to be varied. The first and second distal ends may optionally further include a tip, which is removable or eccentrically located. The dual lumen cannula includes at least one mechanism that, upon actuation, serves to alter the conformation of the first cannula body, the second cannula body, or both the first cannula body and the second cannula body, between a normal profile conformation and a low profile conformation.

When the dual lumen cannula is in use, the normal profile conformation is characterized by the first and second cannula bodies having a lumen diameter at the point of insertion, which is smaller than the lumen diameter both proximal and distal to the point of insertion. The lumen diameters of the first and second cannula bodies distal to the point of insertion are expandable up to the diameter of a surrounding vessel or up to the maximum lumen diameter. The low profile conformation is characterized by the first and second cannula bodies having a lumen diameter at the point of insertion that is greater than the lumen diameter distal to the point of insertion.

The flexible filaments that make up the cannula body of the dual lumen cannula may include one or more materials selected from metals, shape-memory metals, alloys, plastics, textile fibers, synthetic fibers, and/or combinations thereof. Moreover, the at least one mechanism is selected from a mandrel, an electric motor, a change in pressurization, a wrapping string, a balloon and/or a sheath. The first and second cannula bodies of the dual lumen cannula can be positioned coaxially or adjacently.

According to some embodiments, the cannulas may have a small diameter only at the point of insertion. Preferably, the narrow diameter of the cannula occurs over less than 50% of the total length of the cannula, more preferably, less than 40%, more preferably less than 30%, more preferably less than 20%, and most preferably, less than 10%. By "point of insertion" is meant the location where the cannula is inserted into the object to be cannulated. Examples of suitable points of insertion include, but are not limited to, arterial walls; venous walls; the skin; an orifice; the exterior of tubes and containers; and a fixed aperture on a tank or container.

Because of the narrow diameter of the cannula at the point of insertion, the access aperture of the cannula will be small. By "access aperture" is meant the hole that allows the cannula to access the object or vessel to be cannulated, i.e., the hole at the point of insertion.

When used in a medical context, the cannulas can take advantage of the geometry of an individual's vascular tree. Specifically, cannulas are able to compensate for the differences in diameter between access vessels (typically smaller in diameter) and target vessels (typically larger in diameter). To compensate for these differences in diameter, the diameter of the lumen of the high performance cannula is adjustable before, during and after cannulation (i.e., insertion). Specifically, after cannulation the diameter of the cannula either expands to that of the surrounding vessel or environment or returns to its normal profile conformation. In contrast, traditional cannulas are limited by the diameter of the access vessel.

According to some embodiments, the cannulas may include a cannula body having a proximal end, a distal end, and a lumen extending between the proximal and distal ends. The lumen has a diameter, and the cannula is made of a flexible material that allows the diameter of the lumen to be varied. Such cannulas also include means for altering the conformation of the cannula between a normal profile conformation and a low profile conformation, wherein the normal profile conformation is characterized by the cannula having a lumen diameter at the point of insertion and wherein the low profile conformation is characterized by the cannula having a lumen diameter at the point of insertion that is greater than the lumen diameter distal to the point of insertion. Following cannulation, the lumen diameter distal to the point of insertion is expandable to the diameter of the cannulated vessel or to the normal profile conformation diameter of the lumen.

Figure 2A:
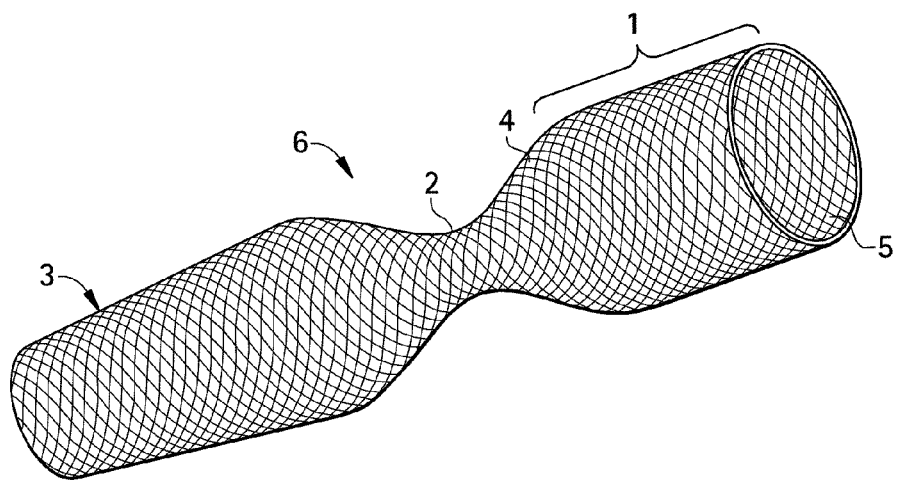
FIG. 2A is a perspective view showing a view of a cannula according to one embodiment in a normal profile conformation when the cannula is in use according to the present methods.

The diameter of the lumen can be varied by altering the cannula between a low profile conformation and a normal profile conformation. By "normal profile conformation" is meant any conformation similar to that shown in FIG. 1A or 2A. According to one embodiment, and as illustrated in FIG. 2A, for example, when the cannula 6 is in use, the normal profile conformation may be characterized by the cannula 6 having a lumen diameter 5 at the point of insertion 2, which is smaller than the lumen diameter 5 both proximal and distal to the point of insertion 2 (e.g., the diameter of the surrounding vessel). Alternatively, as shown in FIG. 1A, the cannula 6 in a normal profile conformation following cannulation can have the shape and diameter of the lumen 5 of the cannula 6 prior to cannulation. In either normal profile conformation, the cannula 6 is characterized by a larger diameter of the lumen 5 as compared to the diameter of the lumen 5 when the cannula is in the low profile conformation.

Figure 2B:
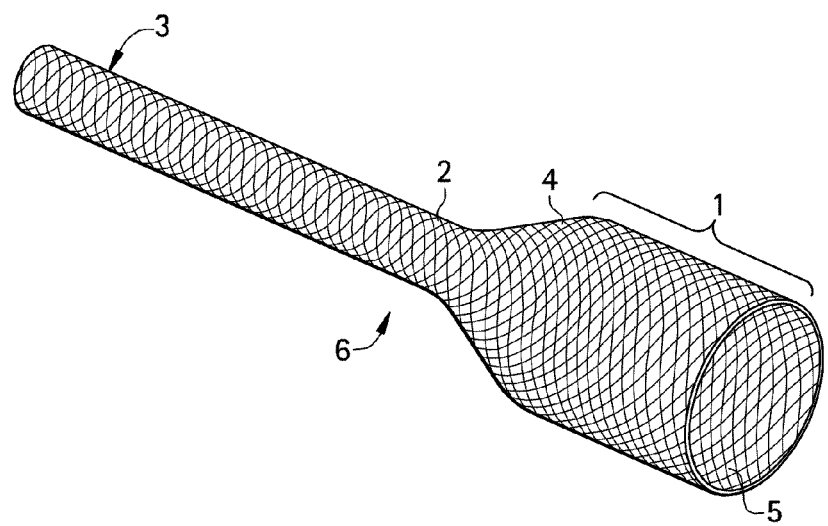
FIG. 2B is a perspective view showing a view of a cannula according to one embodiment in a low profile conformation.
Figure 3A:
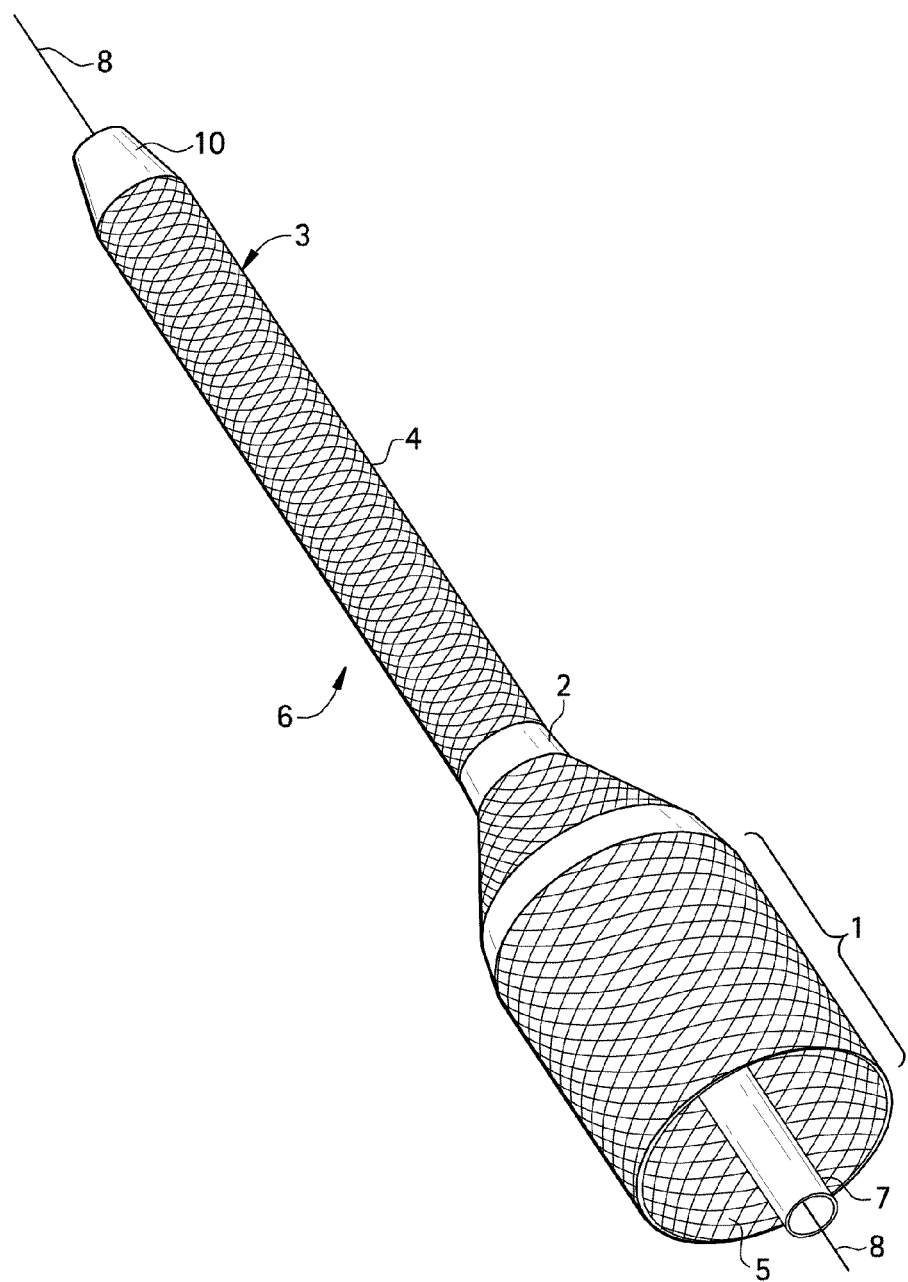
FIG. 3A is a computer-generated drawing showing the high performance cannula according to one embodiment stretched on a mandrel.
Figure 3B:
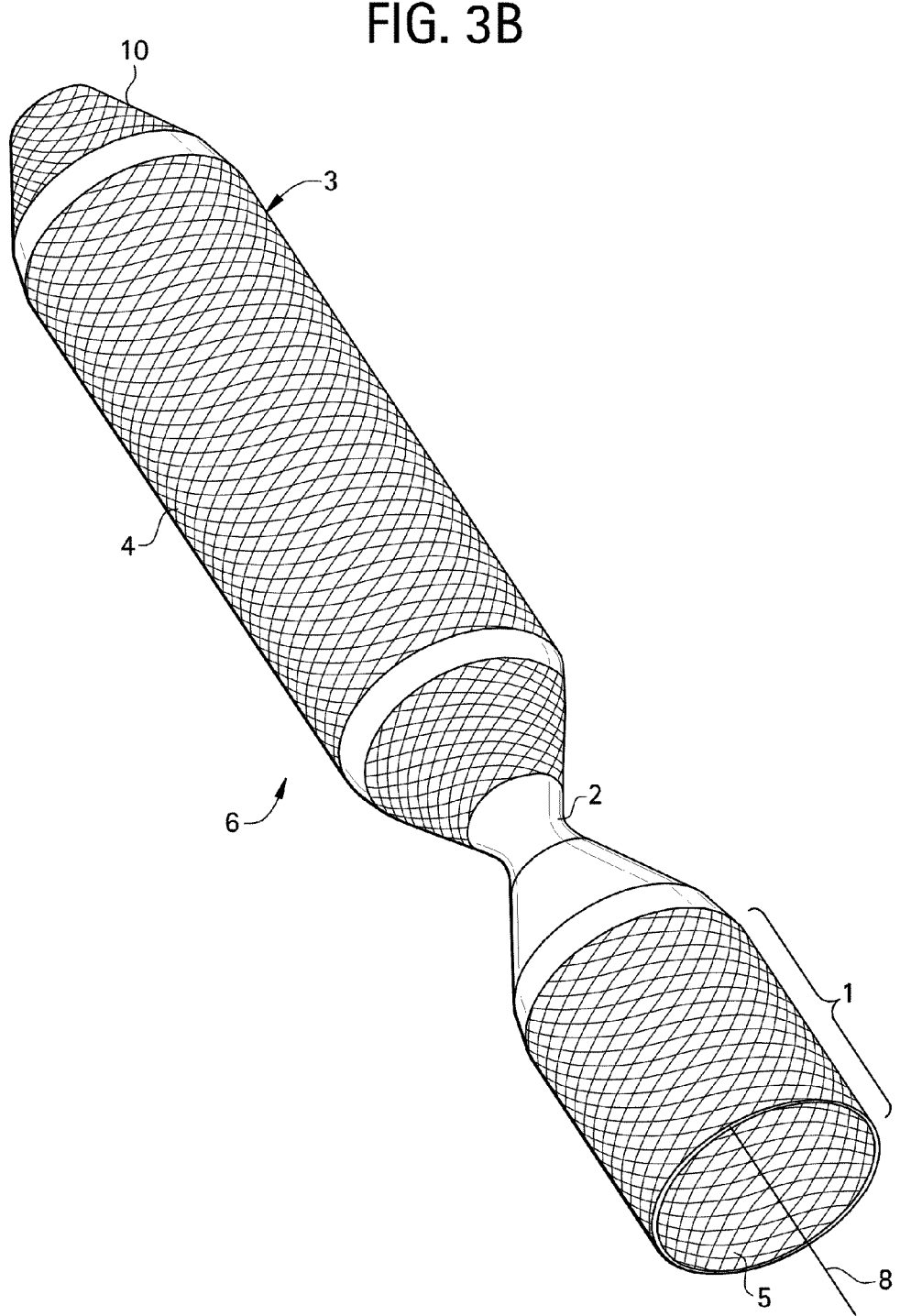
FIG. 3B is a computer-generated drawing showing the high performance cannula according to one embodiment after removal of the mandrel.
Figure 4:
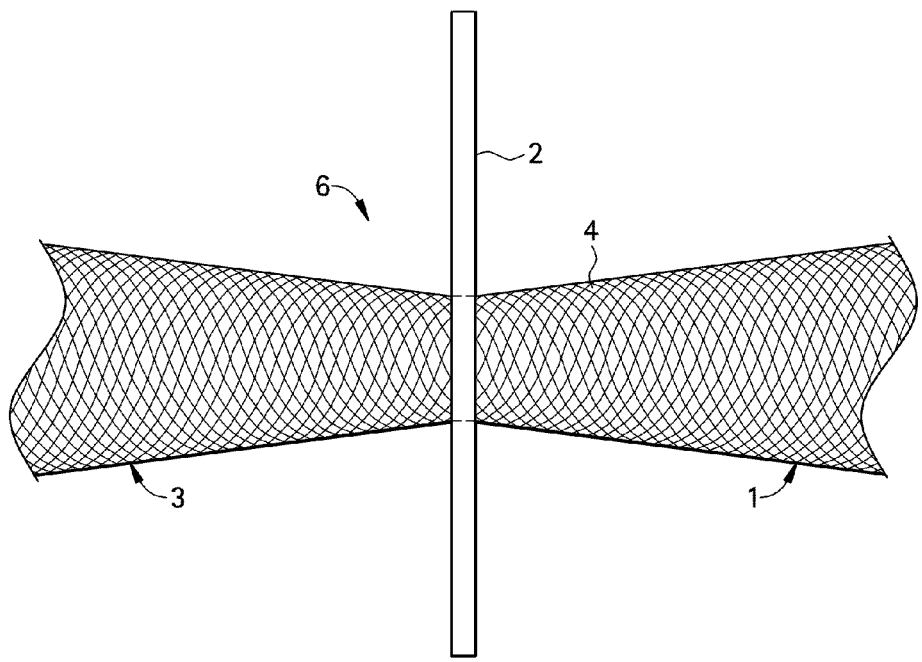
FIG. 4 is a diagram of a prototype high performance cannula according to one embodiment.
Figure 5:
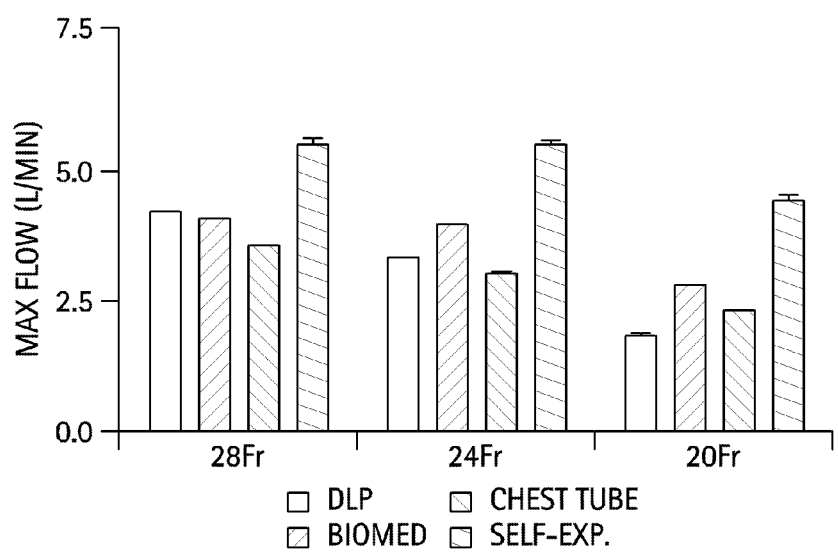
FIG. 5 is a histogram showing the results of in vivo comparison experiments measuring the flow rates through various commercially available cannulas and the high performance cannulas.

By "low profile conformation" is meant any conformation similar to that shown in FIG. 2B. According to one embodiment, illustrated in FIG. 2B, for example, the low profile conformation may be characterized by the cannula having a lumen diameter 5 at the point of insertion 2 that is greater than the lumen diameter 5 distal to the point of insertion 2. In its low profile conformation, a portion of the cannula 6 is characterized by a narrow diameter of the lumen 5 that is suitable for insertion into the object to be cannulated as well as into smaller access vessels. Placing the cannula in the low profile conformation of the cannula 6 can be achieved by the deformation of a shape memory metal, the deformation of an elastic, bendable, moldable, or flexible material; the activation of one or more diameter-varying mechanisms; and the deactivation of one or more diameter-varying mechanisms. One skilled in the relevant art will also recognize that placing the cannula in the low profile conformation can be done before, during, and/or after cannulation.

With any of the cannulas, in the normal profile conformation, the diameter of the lumen 5 at the point of insertion 2 can be narrower than the diameter at the proximal end 1 and/or the distal end 3. The diameter of the lumen 5 at the proximal end 1 and the distal end 3 may be the same or different. Typically, the diameter of the lumen 5 at the distal end 3 is greater than the diameter of the lumen 5 at the point of insertion 2. The diameter of the lumen 5 distal to the point of insertion 2 is either the same as the diameter proximal to the point of insertion 2 (i.e., the diameter of the lumen 5, in the normal profile conformation) or it expands to that of the surrounding vessel or environment.

By "proximal" is meant the external end of the cannula 6 that is not inserted into the object or vessel to be cannulated. Similarly, by "distal" is meant the end of the cannula 6 that is inserted into the object or vessel to be cannulated.

Turning now to the drawings, and to FIGS. 1-4 and 7-9 in particular, various embodiments of the cannula 6 is shown. These cannulas 6 comprise a cannula body 4 having a proximal end 1, a distal end 3, and a lumen 5 having an internal diameter that extends between the proximal end 1 and the distal end 3.

In one embodiment, the cannula 6 is made of a flexible, deformable or moldable material that can be altered to allow the diameter of the lumen 5 to be varied. By "diameter of the lumen" is meant the diameter of the lumen 5 of the cannula body 4.

For example, the cannula body 4 may be made out of a plurality of flexible filaments that allows the diameter of the lumen 5 to be varied. The plurality of flexible filaments may be made of a material such as a plastic, a metal, a shape memory metal, an alloy, a synthetic fiber, a textile fiber, or any combination thereof. Those skilled in the art will recognize that a suitable material may be classified in more than one category. For example, a suitable material can be classified as both an alloy and a shape memory metal. Any of the flexible filaments may be wound into yarn for use. Additionally, the materials may be interwoven or interlaced in any manner such as weaving, braiding or knitting.

The plurality of flexible filaments can contain more than one type of flexible filament. Further, the plurality of flexible filaments can be heterogeneously interwoven or interlaced. For example, the plurality of flexible filaments can be arranged to divide the cannula into segments along any axis such that the segments contain flexible filaments of different materials, or the segments contain the same flexible filaments arranged differently. For example, a cannula can be divided along its length into three or more segments (e.g., a "proximal segment", a "middle segment" and a "distal segment"). In this example, the proximal segment of the cannula body can include textile fiber flexible filaments while the distal segment includes stainless steel flexible filaments in order to provide stronger expansion force at the distal end. A cannula can include any number of segments, or can be unsegmented.

The plurality of flexible filaments can have any shape such as, for example, round, oval, flattened, triangular, rectangular, or any combination thereof. The shape and thickness of the flexible filaments can affect or influence the performance of the cannula. Additionally, the material of the flexible filament may also be spring-loaded or torsioned to further allow the diameter of the lumen 5 to be varied. Specifically, when the material is altered, e.g., stretched, spring-loaded, deformed, activated, compressed, and/or torsioned, the diameter of the lumen 5 is decreased. The diameter of the lumen 5 returns to its normal profile conformation (or to that of the surrounding vessel) upon termination of the alteration.

The plurality of flexible filaments of the cannula body can be made of one or more metals or alloys. Metals or alloys can provide a stronger expansion force (e.g., hoop strength) relative to other materials of the same size such as textile filaments. Because the diameter of metal or alloy flexible filaments can be smaller, while still achieving a certain desired expansion force, a cannula including a plurality of flexible filaments made from metals or alloys can have larger lumens relative to other cannulas having a similar external diameter. Thus, when constructing smaller diameter cannulas, e.g., 1-mm diameter cannulas, it may be preferable to use a plurality of metal flexible filaments such as surgical grade stainless steel. Those skilled in the art will recognize that shape memory metals, such as nitinol, are also able to provide stronger expansion force.

The plurality of flexible filaments can also be made of one or more synthetic fibers. Suitable synthetic fibers include, but are not limited to, rayon, acetate, polyester, nylon, acrylic, modacrylic, olefin, spandex and polypropylene, or combinations thereof.

Likewise, the plurality of flexible filaments can also be made of one or more shape memory metals. The term "shape memory metals" relates to metals and metal alloys that can undergo a solid state phase transformation from one crystal lattice structure to another crystal lattice structure. Because the metal molecules remain in a closely packed structure, the material remains in a solid state. The lower temperature phase is called the Martensite phase and is characterized by the shape memory metal being relatively soft and easily deformable. The higher temperature phase is called the Austenite phase and is characterized by the shape memory metal being relatively stronger. The phase transformation between the Martensite phase and the Austenite phase occurs over a temperature range denoted by the nomenclature:

As=Austenite start temperature
Af=Austenite finish temperature
Ms=Martensite start temperature
Mf=Martensite finish temperature The temperature range of the phase transformation depends on characteristics such as the identity of the alloy and the relative composition. Altering these or other characteristics of the alloy can enhance operation of the cannula. For example, altering the processing of the shape memory metal can change the Austenite start temperature.

The molecular rearrangement of the crystal lattice structure results in two different properties: shape memory effect and superelasticity. The shape memory effect can occur when the shape memory metal is deformed in the Martensite phase. Upon heating above the Austenite finish temperature Af, the shape memory metal undergoes a phase transformation into the Austenite phase, and assumes its original configuration.

Shape memory metals also possess a quality known as superelasticity or pseudoelasticity. Superelasticity occurs to shape memory metals substantially composed of its Austenite form. When a force is imposed on the shape memory metal, there is a phase transformation from the Austenite form to the Martensite form. When the load is decreased, the Martensite form transforms to the Austenite form.

Alloys with shape memory properties include, but are not limited to, nickel/titanium (also known as "nitinol"), copper/zinc/aluminum, copper/aluminum/nickel, silver/cadmium, gold/cadmium, copper/tin, copper/zinc, indium/titanium, nickel/aluminum, iron/platinum, manganese/copper, iron/manganese/silicon, and combinations thereof.

The shape memory and/or the superelastic properties of shape memory metals can be used in the plurality of flexible filaments of the cannula. For example, a cannula comprising flexible filaments made from one or more shape memory metals may be placed in it low profile conformation in the Martensite phase. Upon heating, either by body temperature or by an alternate heating source, the shape memory metal can exist in the Austenite phase and assume the normal profile conformation. In this embodiment, shape memory metals preferably have Austenite finish temperatures slightly less than body temperature. For example, the Austenite finish temperature can be between about 25° C. and 37° C., and preferably between 30° C. and 35° C. Similarly, in this embodiment, the Austenite start temperature is preferably between room temperature and body temperature.

Similarly, in an alternative embodiment, a shape memory metal in the Austenite phase can be placed in the low profile conformation by applying a stress to convert the metal to its Martensite phase. After the cannula is properly placed or inserted, the stress can be relieved and the material of the cannula undergoes a phase transformation to return the cannula to its normal profile conformation in the Austenite phase.

The plurality of flexible filaments of the cannula body can also comprise one or more textile fibers, which include natural or synthetic fibers that can be interlaced to create textiles. Cannulas using textile fibers within the plurality of flexible filaments may be preferable for high-volume and low-cost production of high performance cannulas. Common textile fiber-forming materials include, but are not limited to, cellulosics, e.g., linen, cotton, rayon and acetate; proteins, e.g., wool and silk; polyamides; polyester; olefins; vinyls; acrylics; polytetrafluoroethylene; polyphenylene sulfide; aramids, e.g., Kevlar or Nomex; and polyurethanes, e.g., Lycra, Pellethane and Biomer.

In order to manufacture some textile fibers, polymers can be extruded by techniques such as wet, dry, or melt spinning. The resulting extruded polymer is then processed to obtain the desired texture, shape, and size. By controlling morphology, textile fibers can be manufactured having different mechanical properties. Additionally, the component materials are unique in chemical structure and potential properties. The properties of the cannula can be altered by altering the shape of the textile fiber, the identity of the textile fiber material, the use of monofilaments or multifilaments, the amount of twist binding the textile fibers together, the orientation of molecules in the textile fibers, and the size of the textile fibers.

Flexible filaments used can be converted into yarns using any twisting or entangling processes that can enhance one or more characteristics. As used herein, the term "flexible filaments" also refers to flexible filament yarns. The plurality of flexible filaments can be interlaced by various processes such as weaving, knitting and braiding. Weaving the plurality of flexible filaments relates to interlacing the plurality of flexible filaments at an angle. For example, weaving the plurality of flexible filaments can include interlacing the plurality of filaments at 90° angles. Knitting the plurality of flexible filaments relates to intermeshing loops of the plurality of flexible filaments. Knitted flexible filaments include weft or warp knit flexible filaments. Braiding the plurality of flexible filaments relates to crossing sets of flexible filaments in a diagonal pattern. Braided products can also include tubular structures, with or without a core, as well as ribbon.

Additionally, the woven, braided or knitted pluralities of flexible filaments can be modified to enhance one or more properties. For example, weft-knitted structures are highly extensible when compared with woven fabrics, but they are also dimensionally unstable unless additional yarns are used to interlock the loops and reduce the extension while increasing elastic recovery.

The cannula 6 may also comprise one or more mechanisms that allow the diameter of the lumen 5 to be varied. Such mechanisms may be, for example, coils; springs; extensible, compressible, or releasable wings; foils; folds; and/or cages. However, one skilled in the art will recognize that other suitable mechanisms may also be employed. The cannula may contain at least one mechanism that, upon actuation, serves to alter the cannula between a normal profile conformation and a low profile conformation. For example, when activated, the mechanism can place the cannula 6 in its low profile conformation, thereby decreasing the diameter of the lumen 5. Upon release of the mechanism, the cannula 6 will either return to its normal profile conformation or expand to the diameter of the surrounding vessel or environment. Alternatively, the activated mechanism(s) can maintain the cannula 6 in its normal profile conformation. Thus, in this embodiment, upon release of the mechanism, the cannula 6 is placed in its low profile conformation, thereby decreasing the diameter of the lumen 5.

Suitable mechanisms for altering the diameter of the cannula include, but are not limited to, a mandrel, an electric motor, a nano-engine, a change in pressurization, a wrapping string, a balloon, and a sheath. Those skilled in the art will recognize that these mechanisms may be used alone, or in combination with any other suitable mechanism(s).

When the mechanism is a mandrel, the cannula is placed in its low profile conformation by inserting the mandrel into the lumen of the cannula. After the cannula is appropriately placed or inserted within the object to be cannulated, the mandrel may be removed, thereby allowing the cannula to return to its normal profile conformation.

The mechanism may also be a sheath surrounding the cannula. Those skilled in the art will recognize that keeping the length of the cannula almost constant during expansion of the cannula is one advantage associated with compressing or collapsing the cannula from the outside.

Figure 6A:
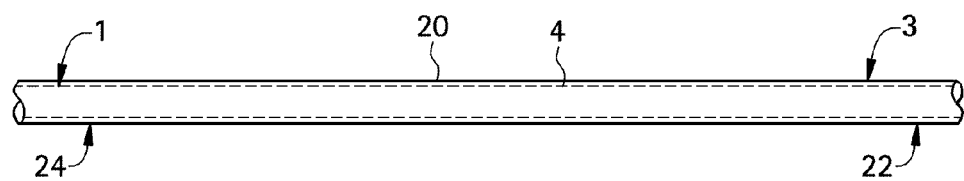
FIG. 6A illustrates a cannula according to one embodiment where the mechanism for altering the diameter of the cannula lumen is a sheath. In this figure, the sheath is positioned around the cannula body, thereby placing the cannula in the low profile conformation.

Referring to FIG. 6A, the cannula 6 is placed in the low profile conformation by placing the cannula body 4 within a sheath 20. The sheath may be any hollow structure that contains and maintains the cannula body 4 in the low profile conformation. For example, the sheath can compress the cannula into its low profile conformation and can provide a smooth outer surface for insertion and withdrawal of the cannula. The sheath can have any geometrical shape including circular, rectangular, oval, hexagonal, octagonal, and the like. The sheath may have a diameter less than the diameter of the cannula body 4 when in its normal profile conformation. Suitable materials for the construction of the sheath include, but are not limited to, polymers such as polyvinylchloride, polyurethane, polyethylene, polypropylene, polyamides; metals; metal alloys; and combinations thereof. The sheath may optionally contain holes and/or may be porous.

Figure 6B:
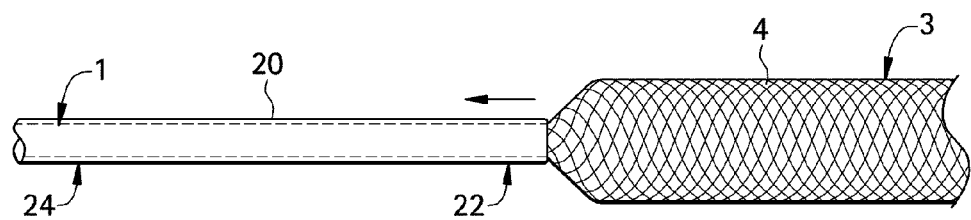
FIG. 6B illustrates a cannula according to the embodiment of FIG. 7A, where the sheath is partially withdrawn from the cannula.
Figure 6C:
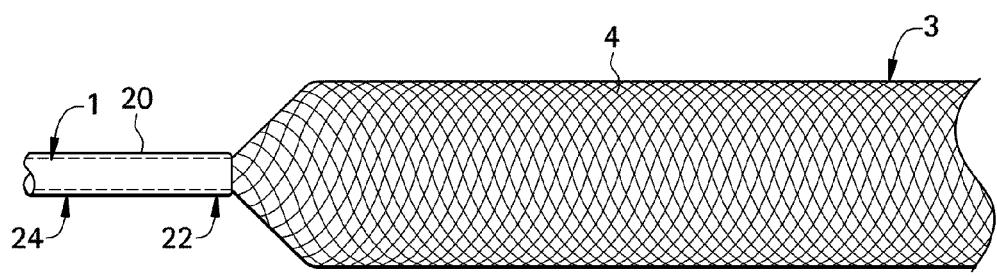
FIG. 6C illustrates a cannula according to the embodiment of FIG. 7A, where the sheath is fully withdrawn from the cannula, and the cannula is in the normal profile conformation.

As shown in FIG. 6A, the cannula 6 is placed into its low profile conformation by compressing, or otherwise containing, the cannula body 4 within the sheath 20. The cannula 6 may optionally have a means for securing the sheath 20 to the cannula body 4. The cannula 6 and sheath 20 are inserted at a point of insertion and the distal end 3 of the cannula body 4 is placed in the appropriate position within the object to be cannulated. Referring to FIG. 6B, the cannula 6 is returned to or placed in its normal profile conformation by withdrawing the sheath 20 proximally, as indicated by the arrow. As the sheath 20 is withdrawn, the distal end 3 of the cannula body 4 expands to the maximum diameter of the surrounding vessel or hollow organ, or to the maximum diameter of the cannula body 4 in the normal profile conformation. FIG. 6C shows the cannula 6 once returned to or placed in its normal profile conformation. Those skilled in the art will recognize that the sheath 20 may be removed by any suitable means known in the art. For example, the sheath 20 can be composed of a degradable or dissolvable material that breaks down after insertion of the cannula 6 in the object to be cannulated. Once the sheath 20 fully degrades or dissolves, the cannula 6 will be returned to its normal profile conformation.

Figure 7A:
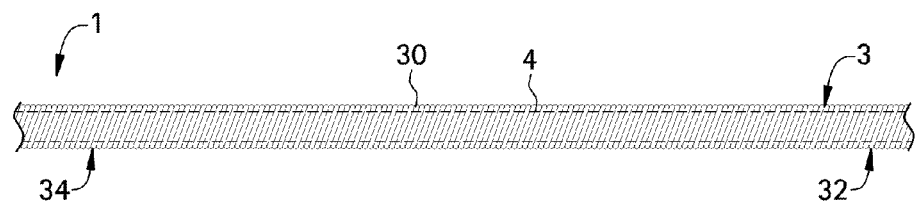
FIG. 7A illustrates a cannula according to one embodiment where the mechanism for altering the diameter of the cannula lumen is a wrapping string. In this figure, the wrapping string is positioned around the cannula body, thereby placing the cannula in the low profile conformation.

The mechanism may also be a wrapping string. Referring to FIG. 7A, the cannula 6 is placed in the low profile conformation by wrapping a wrapping string 30 around the cannula body 4. The cannula body 4 can be wrapped with a wrapping string 30 in any manner such as helically. Further, the wrapping string 30 can overlap, meet edge-to-edge, or have a gap between the loops of the string. In order to return the cannula to the normal profile conformation, the wrapping string 30 is unwound, unwrapped or otherwise removed from the cannula body 4.

Figure 7B:
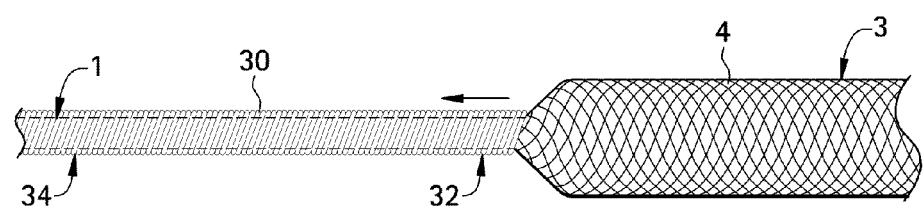
FIG. 7B illustrates a cannula according to the embodiment of FIG. 8A, where the wrapping string is partially withdrawn from the cannula.
Figure 7C:
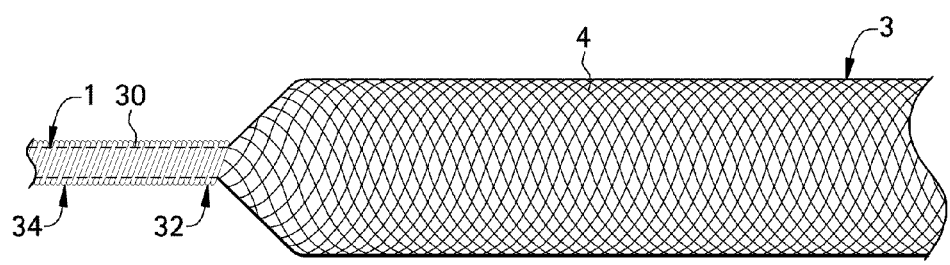
FIG. 7C illustrates a cannula according to the embodiment of FIG. 8A, where the wrapping string is fully withdrawn from the cannula, and the cannula is in the normal profile conformation.

The cannula body 4 can be unwrapped in several ways. Referring to FIG. 7B, the cannula body 4 can be unwrapped in a manner, such that the distal end 32 of the wrapping string 30 remains wrapped around the cannula body 4 and advances towards the proximal end. (e.g., the distal end of the wrapping string is slid proximally) As shown in FIG. 7C, only the distal portion 32 of the wrapping string 30 remains on the proximal portion 1 of the cannula body 4.

Alternatively, the cannula body 4 can be wrapped in a manner such that the distal end 32 of the wrapping string 30 remains wrapped around the cannula body 4 and remains at the distal end 3 of the cannula body 4. As the cannula body 4 is unwrapped, the wrapping string 30 is removed from the proximal end 1 of the cannula body 4. When the cannula body 4 is substantially unwrapped, only the distal portion 32 of the wrapping string 30 remains on the proximal portion 1 of the cannula body 4 following removal.

In yet another embodiment, the wrapping string is configured in such a manner as to unwrap from the distal portion 3 towards the proximal portion 1 of the cannula body 4. As the cannula body 4 is unwrapped, the wrapping string 30 is removed from the distal end 3 of the cannula body 4. When the cannula body 4 is substantially unwrapped, only the proximal portion 32 of the wrapping string 30 remains on the proximal portion 1 of the cannula body 4.

Those skilled in the art will recognize that other suitable means of removing the wrapping string may also be used. The wrapping string may comprise one or more materials such as metal, plastic, synthetic fibers and biodegradable fibers. For example, the wrapping string can comprise a quickly degrading material such that the wrapping string degrades or dissolves after insertion. Additionally, the wrapping string can have any width or thickness consistent with the scale of the object to be cannulated.

Figure 8A:
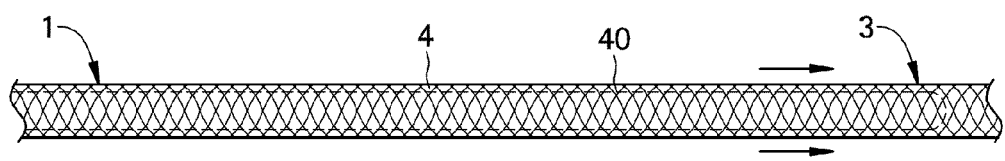
FIG. 8A illustrates a cannula according to one embodiment where the mechanism for altering the diameter of the cannula lumen is a balloon. In this figure, the cannula is in its low profile conformation.
Figure 8B:
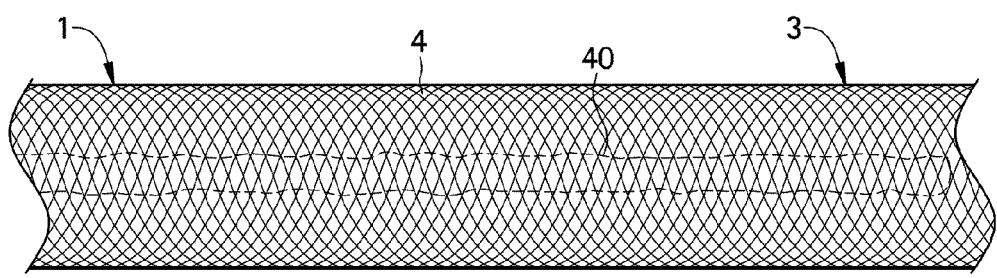
FIG. 8B illustrates a cannula according to the embodiment of FIG. 9A, where the balloon returned the cannula to its normal profile conformation.

The mechanism may also be a balloon. Referring to FIG. 8A, the cannula body 4 is placed in the low profile conformation by inflating a balloon 40, which exerts a force in the distal direction. As the balloon 40 exerts the force, the cannula body changes from the normal profile conformation to the low profile conformation. Referring to FIG. 8B, after the cannula is positioned, the balloon 40 is collapsed and the cannula body 4 returns to the normal profile conformation.

Alternatively, the balloon 40 can be used to return the cannula to its normal profile conformation from the low profile conformation. The cannula body 4 may be placed in the low profile conformation by the actuation of a suitable mechanism. The cannula body 4 is inserted at a point of insertion. When the cannula body 4 is in the appropriate location, the balloon can be inflated in order to return the cannula body to its normal profile conformation. After the cannula body is returned to the normal profile conformation, the balloon may optionally be deflated and removed from the cannula body. Alternatively, the deflated balloon may remain within the lumen.

Those skilled in the art will recognize that the balloon can be any shape as long as the shape allows the balloon to exert a force in the direction necessary to alter the conformation of the cannula. The balloon can be inserted into the object to be cannulated simultaneously with the cannula, or the balloon can be inserted into the lumen of the cannula after the cannula is positioned, or inserted, in the object to be cannulated.

The conformation of the cannula can also be altered by changes in pressurization. For example, the cannula body 4 is placed in the low profile conformation by applying pressure in the distal direction. As the pressure exerts force in the distal direction, the cannula body changes from the normal profile conformation to the low profile conformation. After the cannula is placed or inserted, the pressure is discontinued or altered such that the cannula returns to the normal profile conformation.

Alternatively, pressurization can be used to return the cannula to its normal profile conformation from the low profile conformation. The cannula body 4 may be placed in the low profile conformation by the actuation of a suitable mechanism. The cannula body 4 is inserted at a point of insertion. When the cannula body 4 is inserted in the appropriate location, pressure can be exerted in order to return the cannula body to its normal profile conformation. After the cannula body is returned to the normal profile conformation, the pressure may be discontinued.

The mechanism may also include an electric motor or a nano-engine. The electric motor or nano-engine can be coupled to any suitable mechanism such as, for example, coils; springs; extensible, compressible, or releasable wings; foils; folds; cages; mandrels; balloons; and a sheath. The electric motor or nano-engine can drive the mechanism, which alters the cannula between its low profile conformation and its normal profile conformation. Similarly, the electric motor or nano-engine can be coupled to a device that exerts a force on the cannula to alter the cannula between its low profile conformation and its normal profile conformation. For example, the electric motor or nano-engine can be coupled to a fan that provides pressure that alters the conformation of the cannula.

High-performance cannulas can have plastic properties and/or elastic properties. Additionally, the cannula can be segmented into portions having plastic properties and other portions having elastic properties. As used herein, the term "elastic" relates to materials that deform in a recoverable way until a failure point is reached. Conversely, as used herein, the term "plastic" relates to materials that deform in a non-recoverable manner. A cannula can comprise elastic materials, plastic materials or combinations thereof. Those skilled in the art will recognize that a cannula manufactured from a elastic material(s) can be deformed and will return to its original conformation upon release. Alternatively, a cannula manufactured from a plastic material(s) will not return to its original conformation after deformation. The choice of elastic or plastic material(s) depends on the specific desired function of a particular cannula. For example, a portion of a cannula can be made of a plastic material in order to support the surrounding vasculature, while the remaining portions may be more elastic in nature.

Figure 1C:
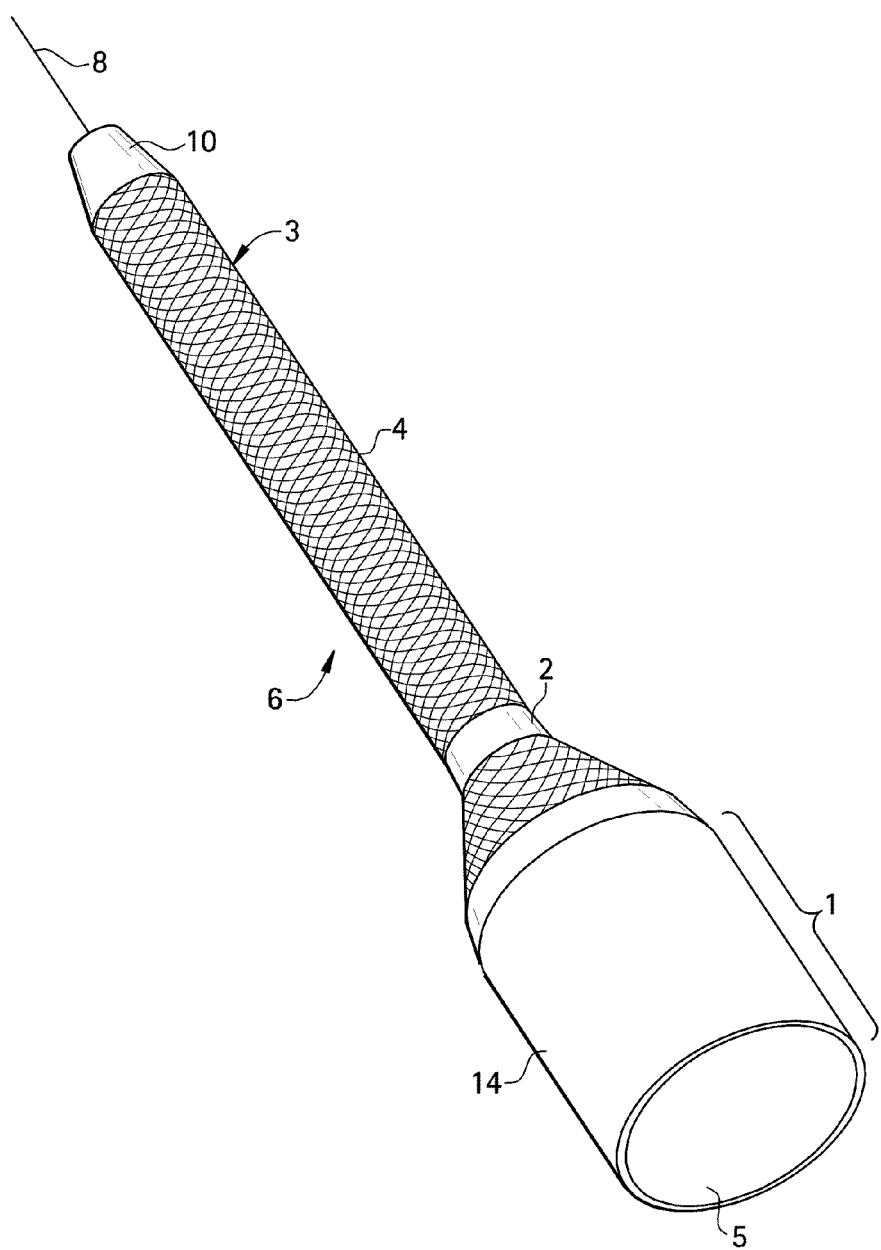
FIG. 1C illustrates a cannula according to one embodiment.

Additionally, at least a portion of the material comprising the cannula body 4 may be coated with a watertight coating. As illustrated in FIG. 1C, a layer 14 of watertight coating is depicted on the surface of cannula 6. For example, the watertight coating can be a plastic (such as plastic). However, those skilled in the relevant arts will recognize that any suitable watertight coating may also be used. In one embodiment, the layer 14 of watertight coating covers the entire cannula body 4. Alternatively, in a separate embodiment, the layer 14 of watertight coating only covers the proximal end 1 of the cannula body 4, or only covers certain segments of the cannula body. For example, the cannula can be designed such that it contains alternating areas of coated and uncoated segments.

Also provided are cannulas having a dual lumen, which can be used to carry two materials. For example, in hemodialysis, a dual lumen cannula can be used such that the lumen of the first cannula body (i.e., "first lumen") can be used for suction (e.g., towards an artificial kidney) and the lumen of the second cannula body (i.e., "second lumen") can be used for reinjection (e.g., return of processed blood towards the patient) or vice versa.

Figure 9:
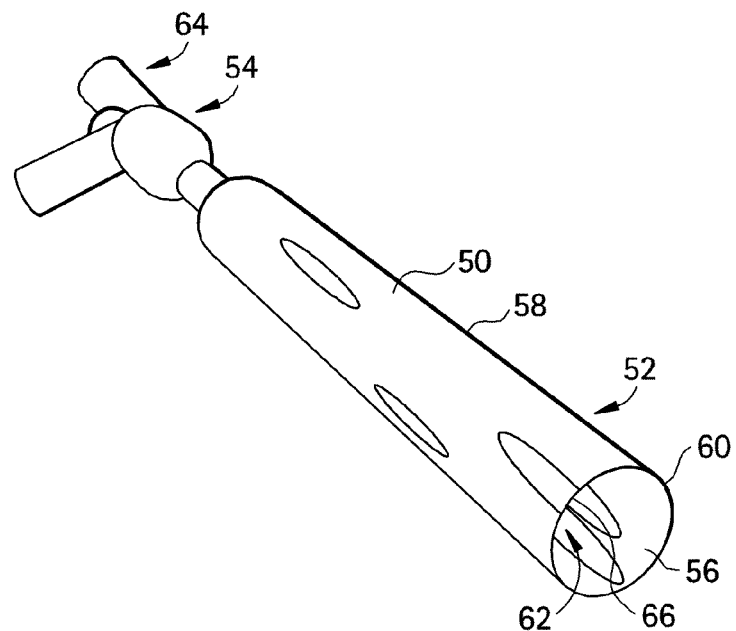
FIG. 9 illustrates a dual lumen cannula according to one embodiment.
Figure 10:
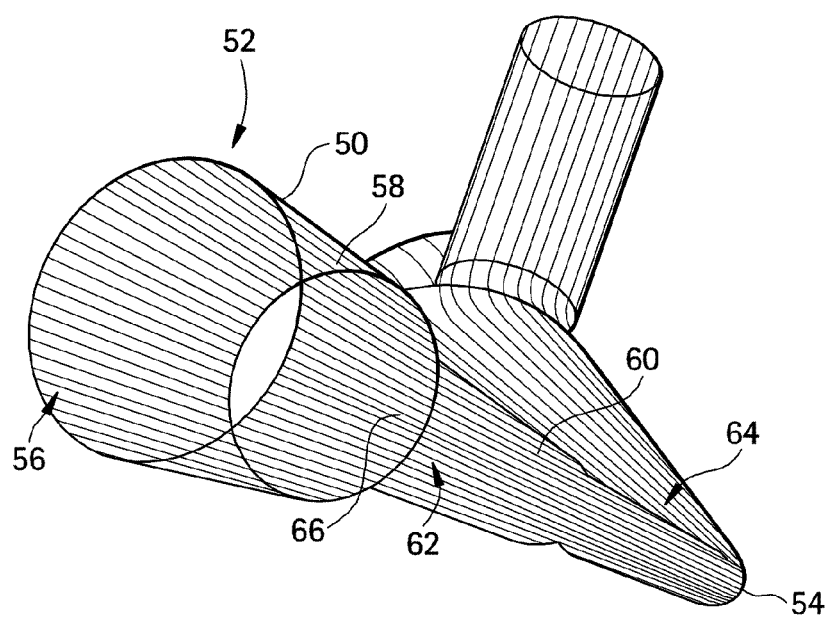
FIG. 10 provides a transparent view of the dual lumen cannula shown in FIG. 10.
Figure 11:
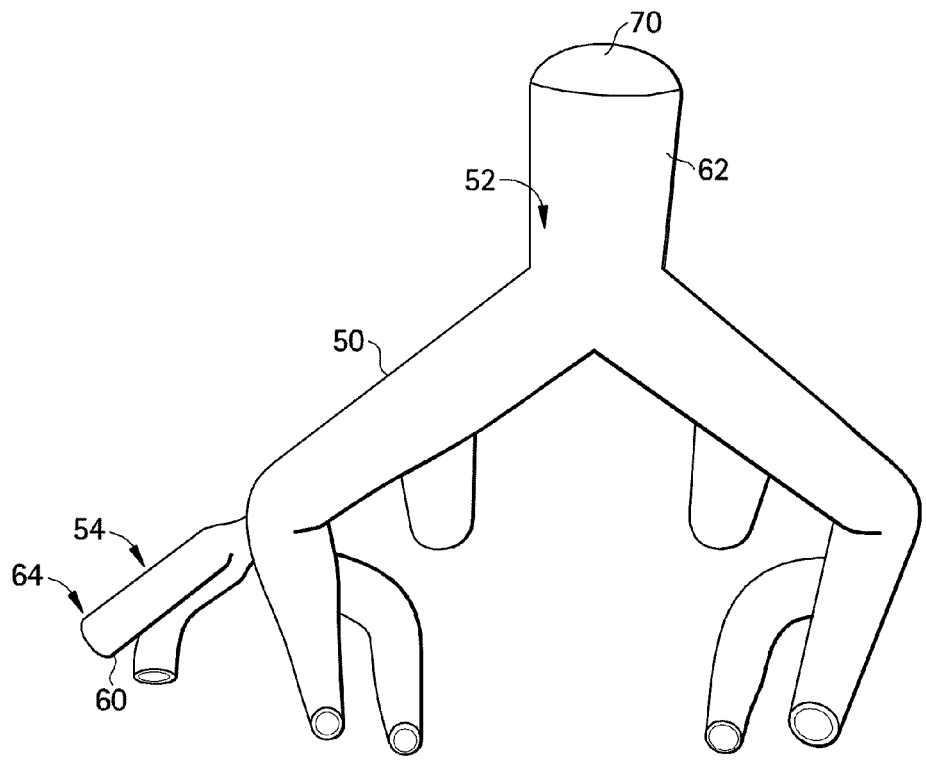
FIG. 11 illustrates the cannula of FIG. 10 in its normal profile conformation after insertion into the vasculature.

The first and second cannula bodies can be positioned coaxially or adjacently. Referring to FIGS. 9 and 10, when the first and second cannula bodies are positioned coaxially, a first cannula body 50, which includes a distal end 52 and a proximal end 54, surrounds a second cannula body 60, which also includes a distal end 62 and a proximal end 64. The distal end 62 of the second cannula body 60 can extend beyond the distal end 52 of the first cannula body 50, or can remain within the first cannula body 50. The second cannula body 60 can be positioned anywhere within the lumen 56 of the first cannula body 50, i.e., the second cannula body 60 can be centered or offset within the lumen 56 of the first cannula body 50. The terms "first cannula" and "second cannula" do not connote orientation. For example, the first cannula body can be the surrounding cannula body or the surrounded cannula body. The first cannula and the second cannula may both be a cannula or one may be a traditional cannula. Preferably, when configured coaxially, the outer cannula is a expandable cannula.

Alternatively, the dual lumens 56 and 66 can be located adjacently rather than coaxially. When located adjacently, the first cannula body 50 and the second cannula body 60 can be the same or different diameters when in the normal profile conformation. Similarly, the lengths of the first cannula body 50 and the second cannula body 60 can be the same or different, and the cannula bodies can be made of the same or different materials.

When located adjacently, a portion of the first cannula body 50 can be coupled to a portion of the second cannula body 60 by any means known in the art including, but not limited to, stitching, adhesive, solder, and/or mechanical coupling. Further, the first cannula body 50 can share at least a portion of its body with the second cannula body 60. This sharing can occur throughout the length of the cannula bodies, intermittently along a length of the cannula bodies, or a single spot on the cannula bodies. Additionally, the first cannula body 50 and second cannula body 60 can be arranged such that they are formed by a septum dividing two sides of a larger cannula body. In such an arrangement, the first cannula body is formed from a portion of the larger cannula body and one side of the septum while the second cannula body is formed from another portion of the larger cannula body and the other side of the septum. Alternatively, there may be two septums within the larger cannula body such that the first cannula body is formed from the larger cannula body and one septum, and the second cannula is formed from the larger cannula body and the other septum.

Further, the first septum can share a portion of its surface with the second septum. This sharing can occur throughout the length or width of the septums, intermittently along the length of the septums, or at a single portion of a surface of each of the septums.

There are various methods of using the dual lumen cannulas described herein. For example, a first cannula can be placed in its low profile conformation, inserted into the patient or object to be cannulated and returned to its normal profile conformation. A second cannula can then be placed inside the first cannula to create two coaxial lumens. Alternatively, the second cannula is collapsed within the first cannula prior to cannulation. Both the first cannula and second cannula can be returned to their normal profile conformation after insertion into the patient or the object to be cannulized. Those skilled in the art will recognize that the same or different mechanisms can be used to alter the conformation of the interior and exterior lumen.

Alternatively, a first cannula can be inserted into a patient and the lumen of the mandrel can be used as second lumen. The outer cannula can be placed in its low-profile conformation and inserted into the patient or the object to be cannulized. Once properly positioned, the cannula is returned to its normal profile conformation. The mandrel used to alter the conformation of the cannula also contains a lumen. After returning the outer cannula to the normal profile conformation, the mandrel is kept within the lumen of the cannula to create a coaxial dual lumen.

Figure 12A:
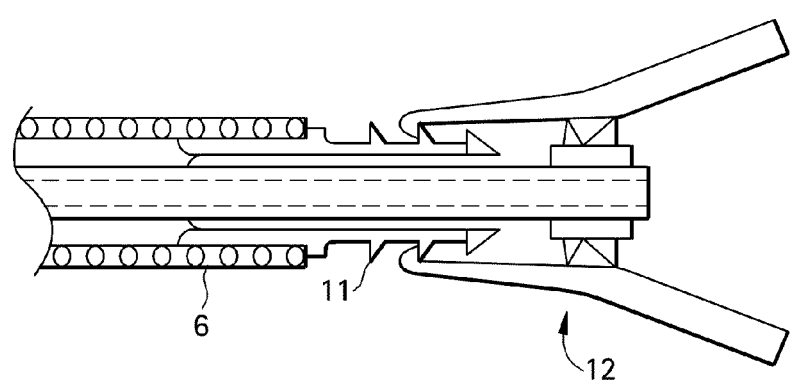
FIG. 12A illustrates a locking mechanism suitable for use with the high performance cannulas.

Any of the high performance cannulas described herein can also include a connector on its proximal end. In FIG. 12A, a cannula 6 is illustrated with connector 11. The connector 11 may be secured with a locking mechanism 12 or a plug. One skilled in the art will recognize that the plug can comprise any shape or material suitable for securing the connector. Alternatively, the connector 11 may be replaced by a flexible (silastic: e.g., 10 cm.) tube, which allows for clamping of the cannula (at the level of the flexible tube) without damage. Additionally, a user could select a connector in accordance with the diameter of the line tubing utilized (cannula-connector line). The proximal end of the cannula may additionally (or alternatively) contain a connecting sleeve rather than a connector. The connecting sleeve can couple the cannula to a perfusion system or other device. The connecting sleeve can comprise any shape, size or material suitable for coupling the cannula to an external device. Additionally, the connecting sleeve may be configured to couple a cannula with a device, wherein the cannula and device have a different diameter, cross-sectional width, and/or size.

According to another embodiment, a mandrel may be mounted on a plug. In some embodiments, the plug is a porous plug. In another preferred embodiment, the plug is a molded plug with a slit for venting. The plug permits the passage of air necessary for venting the cannula. In one implementation, the mandrel is hollow and may be mounted in the plug. The plug may further be perforated so as to allow a guidewire (passing through the cannula tip and into the mandrel) to exit therethrough. The plug, together with the mandrel, preferably fits snugly into the flexible tube (used in place of the connector, as described above) at the cannula end. Hence, the cannula may be collapsed with the plug-carrying mandrel, and may further remain in this configuration due to the snug fit of the plug in the flexible tube.

The cannulas can also include one or more additional devices to increase the functionality and/or performance of the cannula. For example, the cannula can include one or more microturbines, which can provide enhanced capabilities such as increasing the flow rate of fluids through the cannula. The cannulas may also include one or more sensors, which can be coupled to various portions of the cannula to enhance performance or functionality. Sensors coupled to one or more microturbines can be used to adjust and/or maintain the output of the turbine. Similarly, sensors can be coupled to any suitable mechanism that can be used to change or alter the diameter of the lumen. For example, the cannula can include sensors coupled to small electric motors to facilitate telemanipulation of the cannula.

The cannulas may be characterized by a high rate of fluid flow through the lumen 5. Specifically, the rate of fluid flow through the lumen 5 is between 1 mL/min and 100 L/min. Preferably, the rate of fluid flow is between about 100 mL/min and about 6 L/min. When used in connection with cardiac surgery, typical fluid flow rates through the cannula 6 are between about 100 mL/min and 6 L/min. When used during dialysis, or hemofiltration, typical fluid flow rates through the cannula 6 are between about 100 mL/min and about 500 mL/min. When used for intravenous delivery of fluids, typical fluid flow rates through the cannula are between about 1 mL/min and about 10 mL/min. Thus those skilled in the art will recognize that the use of the cannulas is desirable for any application where a continuous fluid flow is required.

The cannulas according to the invention can be a variety of sizes. For example, they can be miniaturized for use in the cannulation of small vessels or objects. Alternatively, they can be enlarged for cannulation of larger vessels or objects. Those skilled in the art will be able to routinely select an appropriate sized cannula.

Arterial Cannulas

One advantage provided by a self-expanding venous cannula (which may be collapsed to a lower profile prior to insertion), is an increase in the volume of blood flow through the cannula coupled with a decreased pressure drop, and a decrease in shear stress. These characteristics are also of interest for efficient blood return via an arterial cannula, which can change its shape once positioned in situ. For a given access aperture on the arterial side, an application of the high flow cannula design described herein (i.e., collapsed insertion and self-expansion in situ) has, in addition to a decreased pressure drop, the additional advantage of diminishing the velocity of the blood jet at the cannula outlet. This reduces the danger of high-velocity jet-lesions of the aortic wall, as well as the potential for aortic wall plaque mobilization and secondary embolization.

Access to the Veins and Arteries

Access catheters are generally necessary for transfusion of fluids, plasma-expanders, blood components or substitutes, and/or for taking measurements. Typical applications include massive volume infusions for patients in circulatory collapse (shock). Under such circumstances, the peripheral target vessels are usually collapsed (e.g., empty due to a lack of circulating blood) and constricted (e.g., due to low cardiac output, centralization, and/or high levels of circulating vaso-constricting agents). Thus, puncturing such collapsed and/or constricted small access vessels may be difficult. Hence, small-bore catheters are usually preferred.

However, one drawback associated with the use of small-bore catheters is that their small luminal diameter may serve to limit flow through the catheter. As such, large-volume transfusions over a short time period may be difficult and/or prolonged, and this may be detrimental for a patient.

To remedy this and/or other drawbacks associated with the use of small-bore catheters, high flow access catheters based on the high flow cannula design described herein (e.g., collapsed insertion and self-expansion in situ) may be used. Specifically, the high flow access catheter may comprise a flexible, elastic plastic catheter that can be stretched over a hollow mandrel in order to be made thinner for introduction over a guide-wire. Upon removal of the mandrel, the catheter will expand to its initial diameter, which may be larger than the diameter at the point of insertion. In some embodiments, the lumen of the catheter may be enlarged (e.g., expanded) over its entire length (either fully or in part).

The high flow access catheter may be stretched over a centrally-positioned mandrel in a number of ways. For instance, the diameter of the tip orifice of the catheter may be smaller than the diameter of the mandrel. Alternatively, other mechanisms (e.g., bars, cams, hooks, etc.) may be used to keep the mandrel within the desired position of the tip of the catheter during loading and insertion. Examples of such mechanisms may include, but are not limited to: (1) a conically shaped tip with central and lateral holes; (2) a two-or-more stage design with or without lateral holes; (3) a tapered design with lateral slits that open when the catheter is expanded or pressurized; and (4) a flexible grid design similar to the one described for the high flow cannulas.

Any suitable mechanisms that allow for increased cross-sectional area of the catheter following insertion may be employed. Such mechanisms may include, but are not limited to, foils, springs, coils, folds or other suitable mechanisms, and those skilled in the art will routinely be able to select a suitable mechanism. Any designs and/or mechanisms, which aid in establishing a shorter, narrow path once the catheter (or cannula) is in its expanded, inserted position may result in higher fluid transfer rates through the catheter (or cannula).

Methods of Making High Performance Cannulas

Cannulas can be manufactured by a variety of methods. For example, the plurality of flexible filaments of the cannula body can be interlaced or interwoven by weaving, braiding or knitting. One skilled in the art will recognize the various automated and non-automated methods for interlacing or interweaving can be employed. The resulting interlaced plurality of flexible filaments can form, for example, a grid- or mesh-like structure that can have its diameter varied.

Alternatively, a similar grid- or mesh-like configuration of a plurality of flexible filaments may be made by etching, cutting or otherwise removing portions of a continuous open-ended body, e.g., a tubular body. For example, the continuous body may comprise materials such as plastic, metal and shape memory metal. Portions of a continuous tube can be removed, by laser-cutting or water-cutting the tube, to create the appropriate grid-like structure. The resulting plastic cannula is expandable to a larger diameter (compared to the diameter in its low profile conformation) in situ.

Alternatively, the cannula can be manufactured by injection molding. The materials comprising the plurality of flexible filaments are liquefied by heating, chemical means or other means, and injected into a suitable molding. Similarly, the cannula body can be manufactured by extrusion. Any of the above manufacturing processes can be combined to create a suitable cannula.

To accelerate the manufacturing process, a photo-activated material may be used for potting the wires or filaments of the grid at a tip of the cannula. For example, the flexible filaments may be potted at the distal end of the cannula with a photo-activated epoxy, which works faster than other potting materials.

DEFINITIONS

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the invention will be apparent from the following detailed description and claims.

For the purposes of promoting an understanding of the embodiments described herein, reference will be made to preferred embodiments and specific language will be used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a composition" includes a plurality of such compositions.

The terms "proximal" and "distal" will be used to describe the opposing axial ends of the inventive closure device, as well as the axial ends of various component features. The term "proximal" is used in its conventional sense to refer to the end of the apparatus (or component thereof) that is closest to the operator during use of the apparatus. The term "distal" is used in its conventional sense to refer to the end of the apparatus (or component thereof) that is initially inserted into the patient, or that is closest to the patient.

EXAMPLES

The following examples are meant to merely illustrate exemplary embodiments of the present disclosure and are not meant to limit any of the embodiments disclosed herein.

Example 1

In Vivo Cannula Comparisons

In vivo experiments in bovine were conducted to compare the flow rate of fluids through the high performance cannula 6 and other commercially available cannulas of various diameters. Specifically, the comparisons involved the cannulation of the superior vena cava (the target vessel) through the jugular vein (the access vessel) after calibration of the aperture (through which the cannula and blood flow have to pass) access to 28 French (9.33 mm), 24 French (8 mm), and 20 French (6.66 mm) cannulas. The cannulas tested included DLP cannulas (Medtronic), Biomedicus cannulas (Medtronic), generic chest tube cannulas, and the high performance cannulas. To insure standardized conditioning, gravity drainage was set at 60 cm of water for each of the cannulas tested.

The results of the comparisons are shown in Table 1.

TABLE 1

| | Comparison A 28 French (9.33 mm) | | | Comparison B 24 French (8 mm) | | | Comparison C 20 French (6.66 mm) | | |
|---|---|---|---|---|---|---|---|---|---|
| | Y | SD | N | Y | SD | N | Y | SD | N |
| DLP cannulas | 4.117 | 0.076 | 3 | 3.317 | 0.076 | 3 | 1.733 | 0.153 | 3 |
| Biomedicus cannulas | 3.983 | 0.046 | 3 | 3.930 | 0.036 | 3 | 2.670 | 0.070 | 3 |
| Chest tube | 3.603 | 0.055 | 3 | 2.947 | 0.117 | 3 | 2.210 | 0.046 | 3 |
| High performance cannulas | 5.350 | 0.132 | 3 | 5.217 | 0.076 | 3 | 4.173 | 0.087 | 3 |

The results depicted in Table 1 demonstrate the flow rate of fluids (Y) in L/min through each of the cannulas tested. The results also show the standard deviation (SD) and number tested (N) for each cannula. For all tested, clinically-relevant cannula diameters (i.e., 28 French, 24 French, and 20 French), the high performance cannulas described herein provided the best flow rate results. The flow rate of fluids through the high performance cannulas was 33-60% higher than the flow rate through the other commonly used, commercially available cannulas. Specifically, for the 20 French outflow vessel, the flow rate with the high performance cannula was superior to the flow rate for the best 28 French cannula (4.117 L/min vs. 4.173 L/min).

Thus, these results demonstrated that the high performance cannulas are superior to the cannulas commonly used by those skilled in the art. These results provided proof of the principle that the flow rate usually generated with a 28 French cannula can also be provided by a high performance cannula requiring only a 20 French hole. The results of these in vivo comparisons are also shown in FIG. 12.

Example 2

Use of High Performance Cannulas

In order to prepare the high performance cannula 6 for use, a mandrel 7 (as shown, for example, in FIG. 3A) is introduced into the cannula 6. Next the cannula 6 is stretched over the mandrel 7 in order to reduce its diameter. Once the cannula 6 is fully in its low profile conformation, it will have a minimal outer diameter.

The vessel to be cannulated is then punctured with the sharp hollow needle. A J-tip guidewire 8 is then introduced into the vessel. Proper positioning of the guidewire is checked by ultrasound, fluoroscopy, or any other suitable means. While keeping the guidewire in place in situ, the needle is then removed from the vessel.

To achieve vessel orifice (e.g., access aperture) dilation, a small (e.g., No. 1) dilator is placed over the guidewire 8 and then removed, while the guidewire 8 remains in place. The access aperture can be redilated using an intermediate (No. 2) dilator that is inserted and removed. Finally, the largest dilator (No. 3) is inserted and removed.

While insuring that the guidewire 8 remains in the proper position, the fully stretched (e.g., low profile conformation) and locked high performance cannula 6 is loaded onto the guidewire 8. This is accomplished by passing the guidewire 8 through the central hole 9 at the tip 10 of the cannula 6 and through the central hole at the tip of the mandrel 7. The cannula 6 is inserted over the wire through the predilated hole in the vessel at the target site.

Once the mandrel 7 is unlocked, the cannula 6 can be pulled back at any time. However, for further advancement, reloading of the cannula 6 onto the mandrel 7 may be necessary. After the mandrel 7 is unlocked, the high performance cannula 6 will expand in situ. Prior to complete removal of the mandrel 7, the position of the cannula 6 should be checked and monitored.

Once an adequate cannula position is reached, the high performance cannula 6 may be secured and the mandrel 7 removed. Finally, the secured high performance cannula 6 can be connected to a line. A mandrel 7 may be used for repositioning, as necessary.

Example 3

Manufacture of High Performance Cannulas

The manufacture of the high performance cannulas may include some or all of the following steps: (a) defining the diameter and length needed; (b) selecting the appropriate materials; (c) preparing the cannula 6; (d) preparing the mandrel 7; and (e) preparing a locking mechanism 12. Additionally, those skilled in the relevant arts will recognize that the high performance cannulas may also be made by any other methods or processes known in the art.

A variety of parameters influence and define the optimal diameter and length configuration of the high performance cannulas. These parameters include target flow, target vessel diameter, target vessel length, target vessel access diameter, target vessel access length, desired covered cannula 6 length proximal to the point of insertion, and/or the desired connector. In one embodiment the cannula 6 can be approximately ⅜" in diameter and 50-70 cm in length, depending on the particular application. Determination of the appropriate diameter and length is within the routine skill of those in the art.

Suitable materials for manufacturing the high performance cannulas can be categorized as cannula size-independent materials and cannula size-dependent materials. Size-independent materials may include, but are not limited to, medical grade polyurethanes (used for potting the cannula tip 10), medical grade silicones (used for covering the portion of the cannula 6 close to the connector 11), and medical grade plastic separating agents. The cannula lumen 5 may contain a spacer that functions to maintain a hole for the guidewire 8 in the potted cannula tip 10.

Cannula size-dependent materials include the interlaced self-expanding wires and/or a plurality of flexible filaments that comprise the cannula body 4. The wires can be made of, for example, a medical grade stainless steel coated with a plastic. Alternatively, an elastic honeycomb structure, a grid, lasercut nitinol, or a plastic scaffold may be used. Other cannula size-dependent materials include molds for potting the cannula tip 10, the connector 11, the mandrel 7, and the locking mechanism 12.

The high performance cannulas 6 can be made with additional working length at both ends of the final cannula 6 dimensions. The interlaced wire bundle at the distal end 3 of the cannula 6 is tied together to a minimal diameter after the insertion of a central spacer wire, which has been treated with a separate form of the potting material. Any excess length can then be removed.

Using a mold prepared with a separating agent, the cannula tip 10 is positioned within the mold. A polyurethane used for potting is mixed, centrifuged, and potted on the cannula tip 10. Following polymerization and unmolding, the spacer is removed, thereby providing a path for the guidewire 8. The tip may be potted using a photoactivated epoxy. Finally, the cannula tip 10 is cut and polished.

Next, the proximal end 1 of the cannula 6 can be coated. Using positioning tools, a partial length dip coating of the proximal end 1 is performed. This dip coating can be a medical grade silicone or any other suitable coating. This coating is then polymerized, and several additional layers can be added. Finally, the proximal end 1 of the cannula 6 can be mounted with an appropriate connector 11. Alternatively (or additionally), various segments of the cannula may be coated (i.e., in an alternating fashion).

In order to prepare the mandrel 7, an adequate diameter of Teflon (or any other flexible (i.e., plastic) rod having a conical tip and a central lumen for the guidewire 8, is used. The length of this rod is then adapted for the length of the high performance cannula 6 to be used.

Figure 12B:
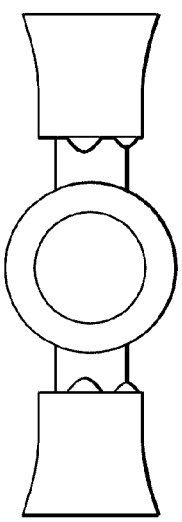
FIG. 12B illustrates one view of a locking mechanism for use with the high performance cannulas.
Figure 12C:
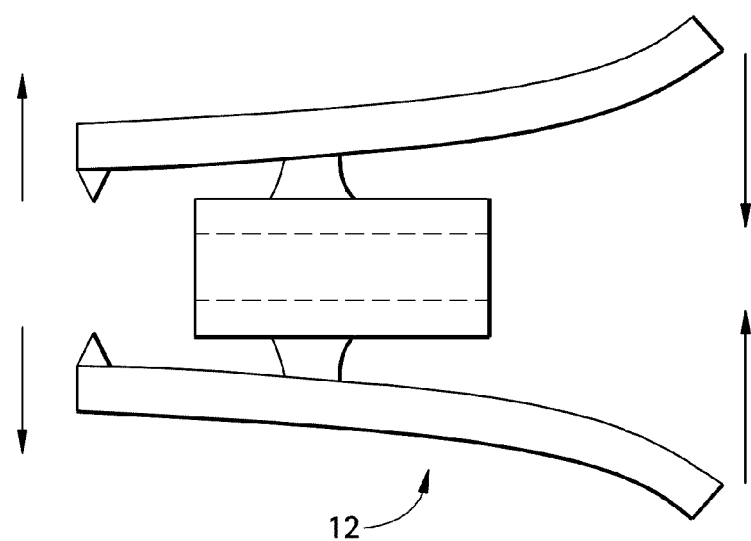
FIG. 12C illustrates another view of a locking mechanism for use with the high performance cannulas.

Finally, the locking mechanism 12 is made by selecting an adequate cap with a locking mechanism that is assembled with the cannula 6. Care should be taken to select a locking mechanism 12 of proper length for the selected high performance cannula 6. An example of an appropriate locking mechanism 12 is illustrated in FIGS. 12A-12C. Alternatively, the connector is capped with a plug. When connecting the cannula to a device such as a perfusion machine, a connecting sleeve is used in place of the connector and locking mechanism. A sleeve capable of coupling the cannula to the machine is selected and placed over the proximal end of the cannula.

Example 4

Temporary Caval Stenting Improves Venous Drainage During Cardiopulmonary Bypass

Figure 13:
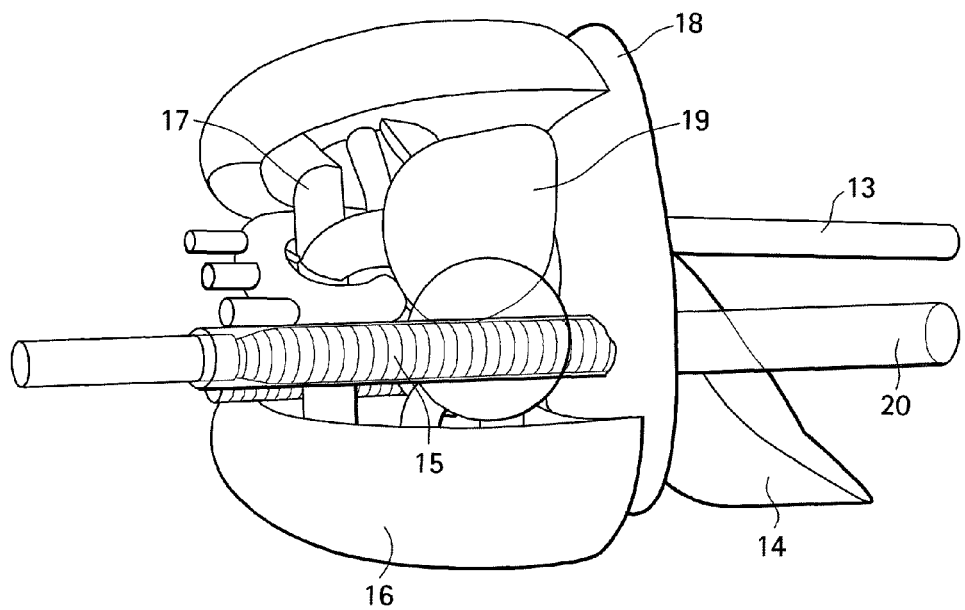
FIG. 13 illustrates an exemplary embodiment of the disclosure, in particular, a schematic view of a short self-expanding cannula: the right atrium is the target position for trans-jugular drainage with remote cannulation. With high drainage load or vacuum, the more distant caval segments can collapse, which in turn impedes blood drainage.
Figure 14:
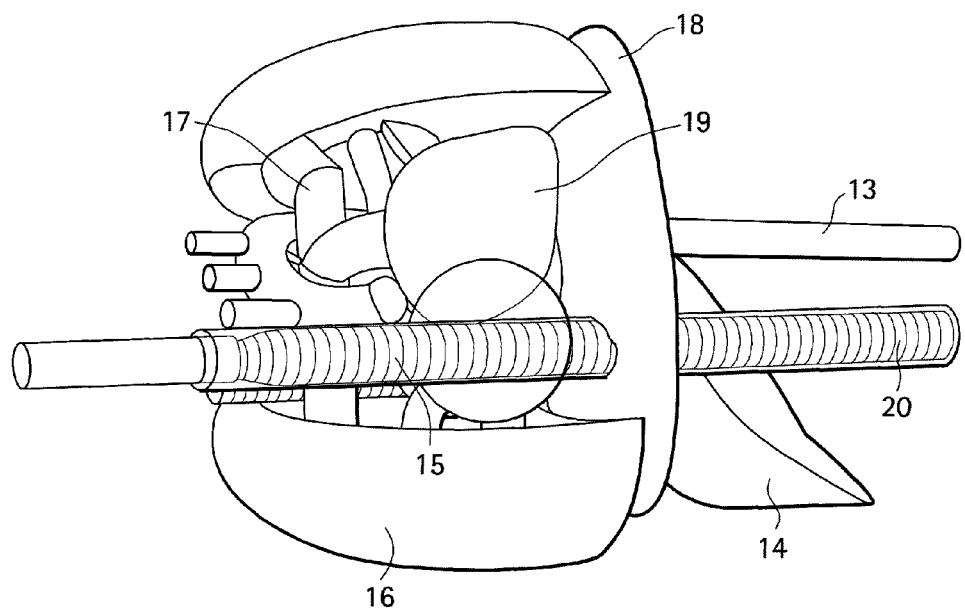
FIG. 14 illustrates an exemplary embodiment of the disclosure, in particular, a schematic view of a long self-expanding cannula used for temporary caval stenting during CPB: the entire caval axis is supported by the venous cannula with open wall design. In addition to the larger diameter of the self-expanding cannula in comparison to traditional cannulas, the open wall of the former also allows the blood to enter the cannula lumen at any level, thus improving drainage.
Figure 15:
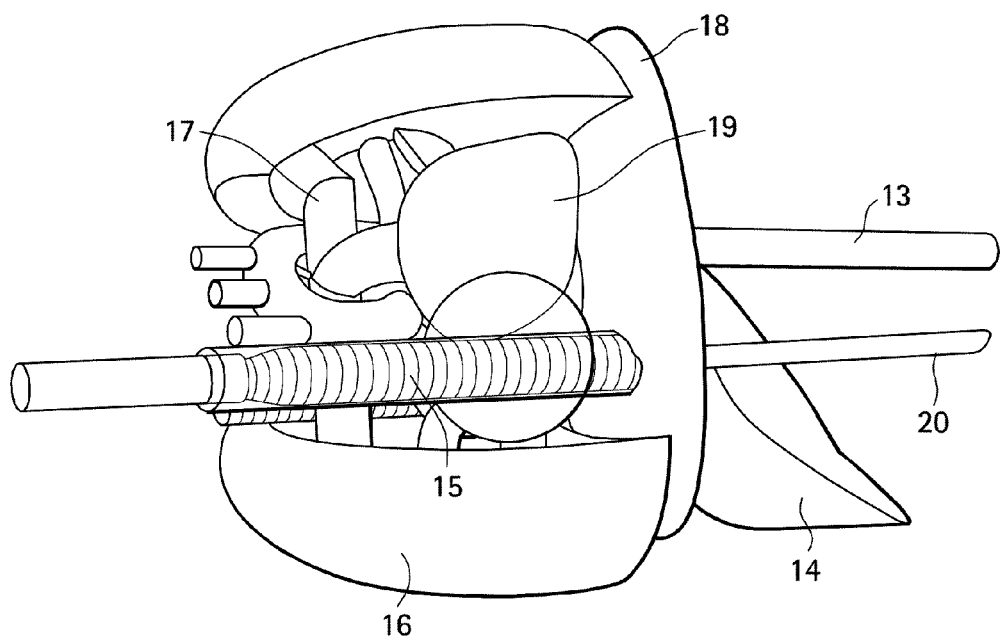
FIG. 15 illustrates an exemplary embodiment of the disclosure, in particular, a schematic view of a short self-expanding cannula under high drainage load: the more distant caval segments can collapse, which in turn impedes blood drainage.

Accordingly, the below detailed example study was designed to assess the potential benefit of temporary caval stenting with short (FIG. 13) versus long (FIG. 14), self-expanding cannulas for remote venous drainage during cardiopulmonary bypass (CPB) with various drainage loads (FIG. 15). FIGS. 13-15 show self expanding cannulas (15) inside the vena cava (20). The heart (19), lungs (16), diaphragm (18), liver (14), aorta (13), and pulmonary artery (17) are also shown.

Animal Preparation:

Following acceptance of the protocol by the state veterinary office, 3 bovine experiments (65±6 kg) were realized under general anesthesia with adjustment of the ventilator parameters as a function of arterial and venous blood gas analyses drawn at regular intervals. Standard monitoring included continuous arterial oxygen saturation, exhaled $CO_2$ concentration, EKG, central venous and arterial blood pressures, as well as continuous measurement of the diameter of the distal vena cava by intravascular ultrasound (Clear View, Boston Scientific).

Cardiopulmonary Bypass:

CPB was established through a cervicotomy for remote jugular vein and carotid artery) cannulation of the right atrium and the caval axis respectively. The tubing set included ½" venous line, a hard shell venous reservoir, a state of the art integrated heat-exchanger/hollow-fiber oxygenator, and a ⅜" arterial line with a 25 μm arterial filter. Clear priming (1500 ml) and full systemic heparinization (heparin loading dose 300 IU/kg body weight, heparin priming dose 5000 IU/l of priming fluid: ACT>480s) were used throughout the procedure.

Exemplary Scenarios Studied:

Maximal stable pump flow which is directly related to venous drainage without augmentation was assessed for remote trans-jugular cannulation of the right atrium/vena cava with standard venous cannulae (43 cm long, wire armed, lighthouse tip design, 28F, dlp, Medtronic) versus self-expanding venous cannulae (43 cm, 53 cm and 63 cm long, Smartcanula®, 18F collapsed for insertion and 36F expanded in situ: Smartcanula LLC, Lausanne, Switzerland) for various table heights. The driving pressure difference or so called drainage load (11) was measured in mmHg as the pressure difference between the level of the right atrium and the blood level in the hard shell venous reservoir. For this purpose, a pressure transducer was positioned at the level of the right atrium and the end of the connected pressure line was positioned at the target blood level in the venous hard shell reservoir. Three different drainage loads (20 mmHg, 25 mmHg, and 30 mmHg) were studied with the help of a motorized table height adjustment system three times for each cannula. Likewise, the inferior vena caval diameters (1 cm above the caval bifurcation) were measured after stabilization of the blood flow with intravascular ultrasound: IVUS (Eur J Vasc Endovasc Surg. 2002 June; 3: 537-542).

Statistical Analyses:

Mean±standard deviation was derived for continuous variables. Paired Student's t-test, respectively surface under the curve was used where applicable for comparison between groups, each animal being its own control.

Figure 16:
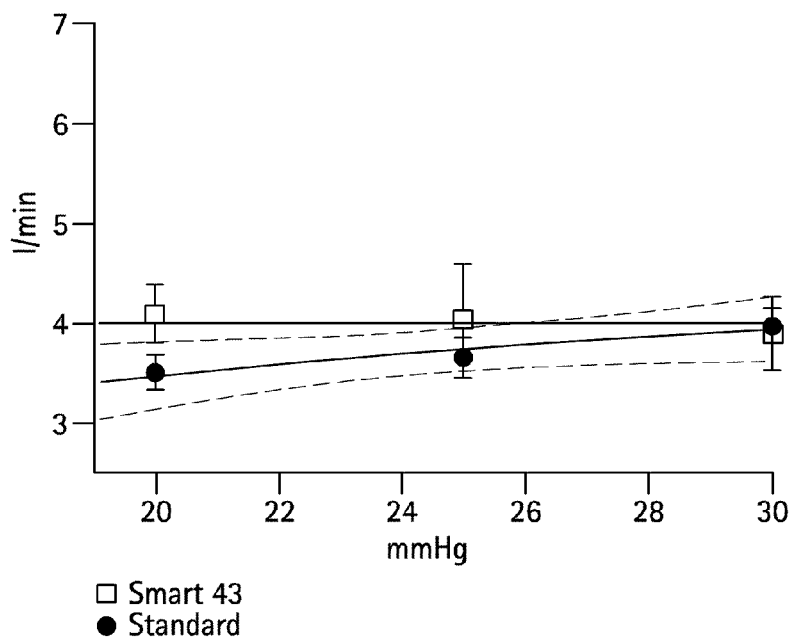
FIG. 16 illustrates an exemplary embodiment of the disclosure, in particular, at low drainage loads, the 43 cm Smartcanula® outperforms the standard wire armed light-house tip cannula.
Figure 17:
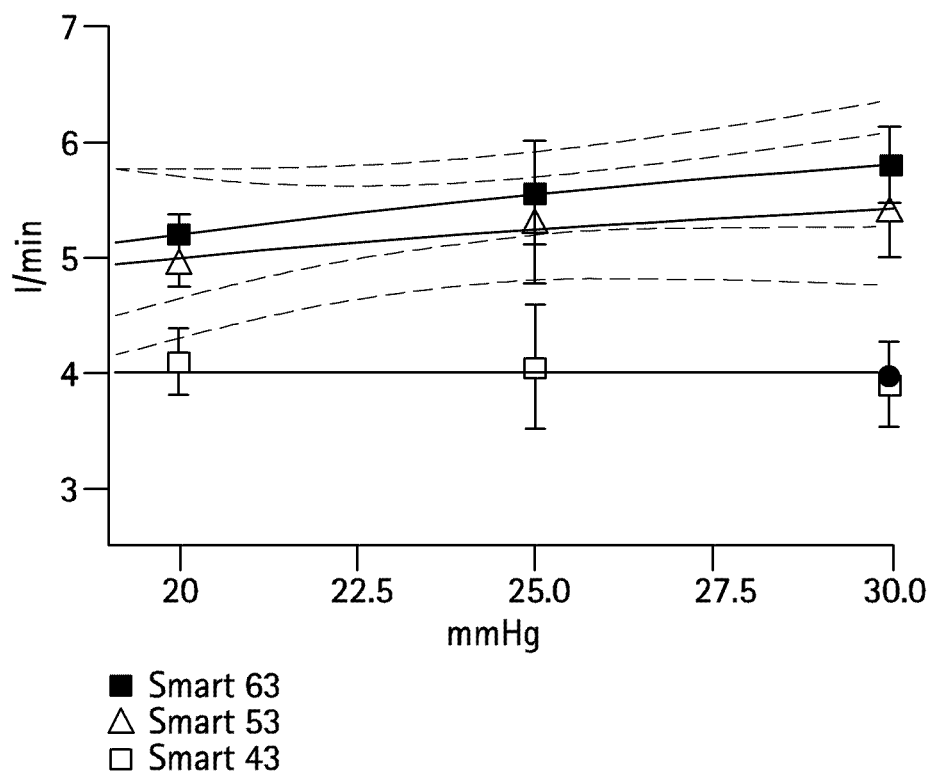
FIG. 17 illustrates an exemplary embodiment of the disclosure, in particular, temporary caval stenting with long venous Smartcanula® cannulas allows for a significant increase of venous drainage and pump flow. The highest flows are achieved with the longest Smartcanula® (63 cm)

Exemplary Results:

Venous drainage (flow in l/min) at 20 mmHg, 25 mmHg, and 30 mmHg drainage load was 3.5±0.5, 3.7±0.7, and 4.0±0.6 for the 28F standard versus 4.1±0.7, 4.0±1.3, and 3.9±1.1 for the 36F Smartcanula® 43 cm (FIG. 16), versus 5.0±0.7, 5.3±1.3, and 5.4±1.4 for the 36F smart 53 cm, versus 5.2±0.5*, 5.6±1.1*, and 5.8±1.0* for the 36F smart 63 cm (FIG. 17). The 43 cm self-expanding 36F Smartcanula® outperforms the 28F standard wire armed cannula at low drainage pressures and without augmentation. However, temporary caval stenting with long self-expanding venous cannulas provides even far superior drainage (+51%).

Figure 18:
FIG. 18 illustrates an exemplary embodiment of the disclosure, in particular, a cross-sectional image of the inferior vena cava achieved with IVUS: in the center the IVUS catheter showing immediately to its left a self expanding venous cannula maintaining the luminal width of the inferior vena cava.
Figure 19:
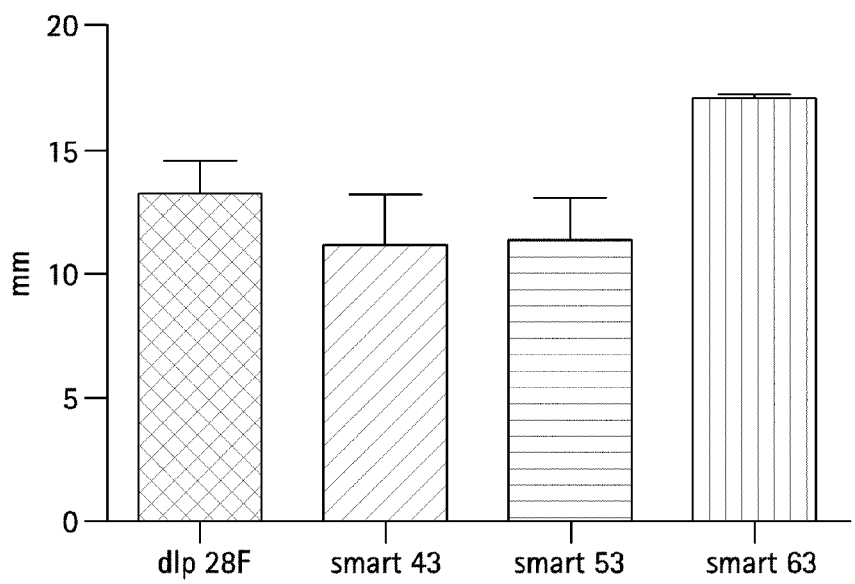
FIG. 19 illustrates an exemplary embodiment of the disclosure, in particular, a cross-sectional diameter of the inferior vena cava achieved with IVUS above the caval bifurcation at 30 mmHg drainage load. The caval diameter decreases with superior drainage, except for the 63 cm self expanding cannula, which is close to the measuring site and maintains the vena cava open.

A typical cross section of the temporarily stented inferior vena cava obtained by intravascular ultrasound are shown in FIG. 18. The self-expanding venous cannula maintains the luminal width at the level of the IVUS probe. FIG. 19 displays the inferior vena caval diameters at 30 mmHg: 13.5±4.8 mm for 28F standard, 11.1±3.6 36F smart 43 cm, 11.3±3.2 for 36F 53 cm, and 17.0±0.1* for 36F 63 cm (*=p<0.05 for 28F standard versus 36F smart 63 cm long).

Increased venous drainage with gravity alone can be achieved by temporary stenting of the caval axis with the long self-expanding venous Smartcanula®, which prevents the floppy venous wall from collapsing during CPB. It has been previously noted, that self-expanding venous cannulas allow for superior venous drainage with little augmentation (and, in some embodiments, preferably without any augmentation) in comparison to standard wire supported light-house tip cannulas (Interactive CardioVascular and Thoracic Surgery 2002; 1: 23-27) as well as traditional thin-walled percutaneous venous cannulas (Ann Thorac Surg. 2002 October; 74: S1330-3), and similar results have been noted for the clinical setting (Eur J Cardio-thorac Surg 2008; 34:635-640.).

The 43 cm self-expanding 36F Smartcanula® provided for in the present example embodiments provides for better venous drainage (+17%) at low drainage loads (20 mmHg), and without augmentation, than the 28F standard wire armed cannula (FIG. 16). The flow achievable with the self-expanding venous cannula at 20 mmHg drainage load is difficult to improve further (e.g., by increasing the table height and providing 25 mmHg drainage load and 30 mmHg respectively). The venous blood that can reach the cannula easily, may be drained directly to the venous reservoir already with 20 mmHg drainage load. In contrast, increasing the table height improved the venous drainage with the control cannula, indicating that the standard lighthouse tip cannula itself may be limiting venous drainage, and that this problem linked to the pressure drop can be overcome up to some point by increasing the drainage load, i.e. the table height.

These results show that longer self-expanding venous cannulas provide better venous drainage than shorter ones. As one of skill in the art will appreciate, this is against traditional wisdom which implies, that longer cannulas have higher resistance, and therefore, lower flow or drainage capacity respectively. It has been understood that such a phenomenon is explained by the fact that longer traditional cannulas are in fact long narrow tubes, and therefore the resistance increases indeed in linear fashion with cannula length (Bernoulli's law), at least as long as laminar flow patterns can be maintained.

In contrast, the self-expanding venous cannulas (e.g., Smartcannula®) act only as somewhat restrictive narrow tubes for the first few cm within the access vessel (e.g., the jugular vein). For the remainder of the vein (e.g., the superior vena cava, the right atrium and/or the inferior vena cava), the self-expanding venous cannulas not only adapt to the larger venous diameter and are therefore less limiting to the flow because of the superior mean cross-sectional area, but in addition, allow for direct entrance of collateral blood inflow into the cannula lumen. Therefore, in some embodiments, a full blood flow uses only the last few centimeters of the self-expanding cannula before it exits from the body, whereas elsewhere, the cannula flow is only a fraction of the total blood flow. Again, this drainage pattern according to some embodiments is very different from that observed in traditional percutaneous cannulas, where the entire blood flow passes through the narrow cannula lumen over its entire length either because (according to some embodiments) there are orifices only at the cannula tip, or because the venous wall is sucked into additional orifices positioned within the vein.

The open wall design of the Smartcanula®, over the vast majority of its surface, has the additional advantage of being used as a temporary caval stent and thus, and, in some embodiments, prevents the collapse of the vena cava (FIG. 6), which is a major limitation for efficient drainage as demonstrated by the fact that the longest self-expanding venous cannula (63 cm) used in one of the illustrated exemplary embodiments disclosed in the subject application provides up to (for example) 51% more venous drainage/pump flow as compared to the short 43 cm version.

Moreover, the technique for temporary caval stenting demonstrated may be fully reversible. For example, a completely expanded 36F self-expanding cannula (the most frequently used size in adults) does not reach the natural diameter of the caval veins in adults which measure usually 60F or more. In some embodiments, if it is true that the self-expanding cannula may act as a spacer during perfusion, thus preventing the caval veins from collapsing, and therefore the venous wall touches the cannula, it has to be considered that this also may happen with traditional cannulas at the cannula site, as well as (for example) at the non-supported sites as demonstrated routinely by the so-called atrial chatter (The Heart Surgery Forum 2005; 8: E241-245; Artif Organs. 1991 February; 15(1):35-41).

One of skill in the art will appreciate that the diameter of the inferior vena cava measured above its bifurcation appears to decrease with improved venous drainage by almost 20% (for example) for 43 cm and 53 cm self-expanding cannulas as compared to the standard rectilinear light-house tip designs (FIG. 7). In contrast, for example, there is a 25% increase in diameter with reference to the 28F reference diameter for the 36F 63 cm self-expanding design (p<0.05), for example, or a 54% increase with reference to the 36F 53 cm self-expanding design (for example). This increase of the inferior caval diameter with the longest self-expanding cannula is due to the proximity of its proximity to the level of the measurement.

A different problem is the removal of a temporary caval stent (i.e., cannula). Fortunately, this appears to be a minor issue. In some embodiments, the self-expanding cannula is collapsed prior to insertion by stretching it with the corresponding mandrel. Likewise, gentle traction at decannulation results in elongation, and therefore reduces the diameter. This in turn makes the removal of the "temporary caval stent/self expanding cannula" according to some embodiments less traumatic than with traditional rectilinear cannulas, which tend to stick to the vessel wall. In some embodiments, withdrawal of the self-expanding cannula may be accomplished by stretching the cannula (preferably completely) between two fingers positioned at the vascular entry site; this is done in order to prevent the blood from exiting at the same time.

Thus, according to some embodiments, as disclosed above, temporary stenting of the caval axis during CPB by the means of long, self-expanding venous cannulas provides improved venous drainage, in some cases up to 51% (or more) above the traditional values utilizing prior techniques. In some embodiments, gravity drainage with low drainage loads may be sufficient and augmentation with centrifugal pumps, vacuum or other adjuncts may not only unnecessary, but appears to be flow limiting.

Example 5

Dual Temporary Caval Stenting Improves Venous Drainage During Total Cardiopulmonary Bypass Objectives:
Switching from partial to total cardio-pulmonary bypass (CPB) often results in major loss of circulating volume, which in turn can jeopardize adequate systemic perfusion. The present study was designed to assess the potential benefit of dual temporary caval stenting during partial and total CPB.
Methods:
Open chest perfusion and bi-caval cannulation was realized in bovine experiments either with traditional angled metal cannulas (DLP, Medtronic, Minneapolis, USA: 24F and 28F) having a fixed geometry versus self-expanding cannulas (Smartcanula LLC, Lausanne, Switzerland: 18/36F 260 mm and 18/36F 430 mm) allowing for dual temporary caval stenting in bovine experiments (65±6 kg). Maximal pump-oxygenator flows were assessed in random fashion for partial (caval veins un-snared) versus total bypass mode (caval veins snared) at 20, 30 and 40 mmHg of driving pressure using a motorized operating table height adjustment system.
Results:
Initial venous drainage (flow in l/min) at 20 mmHg (30 mmHg; 40 mmHg) in partial CPB mode accounted for 4.47+0.34 (4.52+0.55; 4.61+0.98) for standard versus 4.93+0.50 (5.22+0.27; 4.28+0.88) for temporary caval stenting=110% (115%; 93%). For total CPB (caval veins snared) the venous drainage accounted for 2.25+0.14 (2.15+0.57) for standard versus 3.59+0.7 (3.70+0.60) for temporary caval stenting=156% (172%): =p<0.05 for standard versus temporary caval stenting.
Conclusions:
The 18/36F self-expanding Smartcanulas® outperform the standard angled metal cannulas during partial bypass with low drainage load (+10-15%) and even more so during total bypass (+56-72%). Further improvements may be achieved with longer self-expanding cannulas for temporary venous stenting.

Example 6

Central Use of Long High Performance Cannulas

Series of porcine experiments with central cannulation (right atrium into inferior vena cava).

Standard approach is based on so called two stage cannulas which inserted through the right atrium with their tip (typically lighthouse tip, size 29F-36F) placed at the level of the intra-hepatic inferior vena cava and a second larger basket at the level of the right atrium (typically size 37F-48F) and connecting to ½" tubing.

In this study such a traditional two stage cannula (RMI, 29/37F 34 cm long; manufactured by Edwards Lifesciences) was compared to 30/45F self-expanding cannulas (insertion size 30F, expands to 45F within the inferior vena cava: Smartcanula LLC, Lausanne, Switzerland) with two lengths, namely 43 cm and 53 cm.

Various drainage loads were study for the three different cannulas. The main finding of the pooled data can be summarized as follows:

A) the 43 cm self expanding cannula reaches a higher flow already with low drainage loads (20 mmHg: cross sectional area=78.5 mm2) as compared to the standard two stage cannula, and this despite the fact, that the access orifice is only 10 mm in diameter as compared to 12.33 mm of the standard RMI cannula (cross sectional area=119.4 or 152% of the self expanding cannula).

B) the 53 cm self expanding cannula reaches even higher flows for both low drainage loads (20 mmHg: cross sectional area=78.5 mm2) and higher drainage loads (30 and 40 mmHg: 127% overall) as compared to the standard two stage cannula, and this despite the fact, that the access orifice is only 10 mm in diameter as compared to 12.33 mm of the standard RMI cannula (cross sectional area=119.4 or 152% of the self expanding cannula).

Figure 20:
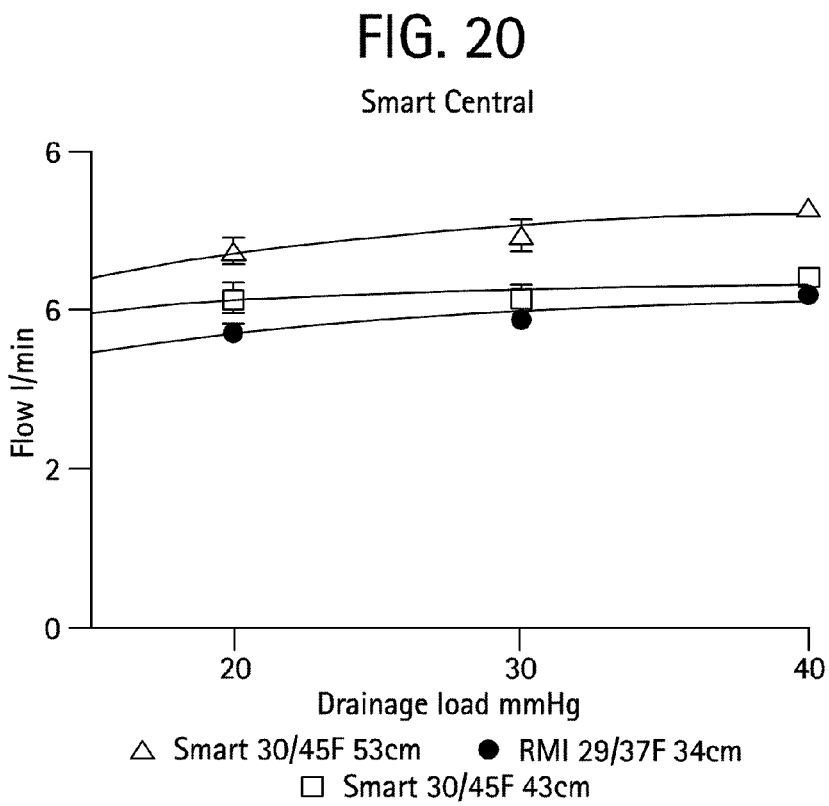
FIG. 20 shows central (right atrial) cannulation down into the inferior vena cava used in the in vivo evaluation of venous drainage for the standard RMI two stage cannula (bottom curve) and two self expanding cannulas with smaller access diameter and 43 cm and 53 cm length, respectively.
Figure 21:
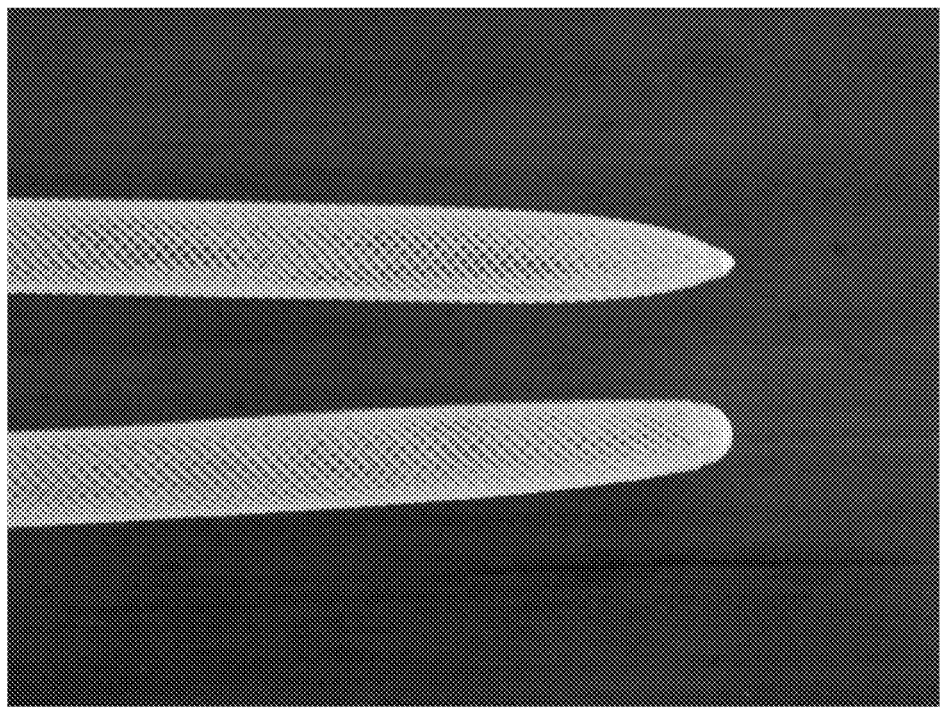
FIG. 21 illustrates the tip manufacturing, which has been potted in the past for stainless steel wire braid, but may also be formed by ultra-sonic welding for the textile version.
Figure 22A:
FIGS. 22A and 22B illustrate the other end of the cannula (silicone sleeve for connection to the tubing of the pump->oxygenator) that may be compression molded (FIG. 22A) or injection molded (FIG. 22B). Both of these techniques can be used for metal and textile braids.
Figure 22B:
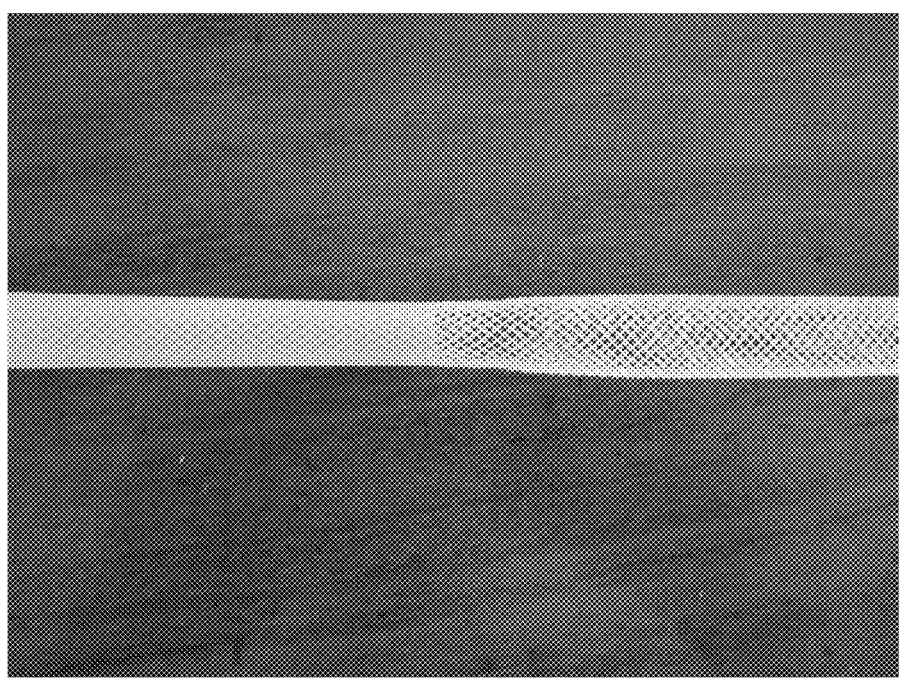

See FIG. 20.

In vivo evaluation of venous drainage for the standard RMI two stage cannula (bottom curve) and two self expanding cannulas with smaller access diameter and 43 cm and 53 cm length respectively. The 43 cm self expanding cannula outperforms the standard two stage cannula mainly for low drainage loads (20 mmHg) whereas the 53 cm version provides superior flows at low and higher drainage loads.

Example 7

In Vivo Cannula Comparisons

In vivo experiments in bovine were conducted to compare the flow rate of fluids through the two rectilinear cannulas. The first cannula was a rectilinear wall-less cannula and the second cannula was a rectilinear cannula with a lighthouse tip.

The results of the comparisons are shown in FIG. 23.

The results depicted in FIG. 23 demonstrate the flow rate of fluids (Y) in L/min through each of the cannulas tested. The results also show the standard deviation (SD) for each cannula. For all tested, the wall-less cannulas described herein provided the best flow rate results. The flow rate of fluids through the high performance cannulas was higher than the flow rate through the lighthouse tipped cannulas.

Thus, these results demonstrated that the wall-less cannulas are superior to the lighthouse tip cannulas commonly used by those skilled in the art.

REFERENCES

The following references, referred to above, are listed below; each of which, in its entirety, is herein incorporated by reference in subject application:
Antonio F. Corno. "Systemic venous drainage: can we help Newton?" Eur. J. Cardiothorac. Surg., June 2007; 31: 1044-1051.
Matthias E. W. Kirsch, Zannis Kostantinos, Firas Ali, Emmanuelle Vermes, Gerard Bajan, and Daniel Y. Loisance; "Kinetic assisted venous drainage for orthotopic heart transplantation in patients under mechanical circulatory support: a double-edged sword"; Eur. J. Cardiothorac. Surg., March 2008; 33: 418-423.
Tevaearai H A T, Mueller X M, Jegger D, Ruckat P, von Segesser L K; "Venous drainage with a single peripheral bicaval cannula for less invasive atrial septal defect repair"; Ann Thorac Surg 2001; 72: 1772-1773.
Mueller X M, Tevaearai H T, Horisberger J, Augstburger M, Burki M, von Segesser L K; "Vacuum assisted venous drainage does not increase trauma to blood cells"; ASAIO J 2001; 47: 651-654.
von Segesser L K (2006); "Peripheral cannulation for cardiopulmonary bypass"; Multimedia Manual of Cardiothoracic Surgery doi:10.1510/mmcts.2005.001610.
von Segesser L K (1999); "Cardiopulmonary support and extracorporeal membrane oxygenation for cardiac assist"; Ann Thorac Surg 68: 672-677
Jegger D, Tevaearai H T, Mueller X M, Horisberger J, von Segesser L K; "Limitations using the vacuum-assist drainage technique during cardiopulmonary bypass procedures"; J Extra-Corpor Technol 2003; 35: 207.
Mueller X M, Mallabiabarena I, Mucciolo G, von Segesser L K; "Optimized venous return with a self-expanding cannula: from computational fluid dynamics to clinical application"; Interactive CardioVascular and Thoracic Surgery 2002; 1: 23-27.
von Segesser L K, Jegger D, Mucciolo G, Tozzi P, Mucciolo A, Delay D, Mallabiabarena I, Horisberger J.; "The Smart Canula: a new tool for remote access perfusion in limited access surgery"; The Heart Surgery Forum 2005; 8: E241-245.
von Segesser L K, Ferrari E, Delay D, Horisnberger J, Tozzi P. Herzentlastung mittels EKZ vor der Resternotomie. Z. Herz-, Thorax-, Gefasschirurgie 2007; 21: 1-7.
Ni Y, Leskosek B, Shi L, Chen Y, Qian L, Li R, Tu Z, von Segesser L K; "Optimization of venous return tubing diameter for cardiopulmonary bypass"; Eur J Cardio-thorac Surg 2001; 20: 614-620
von Segesser L K, Marty B, Ruchat P, Bogen M, Gallino A; "Routine use of intravascular ultrasound for endovascular aneurysm repair: angiography is not necessary"; Eur J Vasc Endovasc Surg. 2002 June; 3: 537-542.
Mueller X M, Tevaearai H T, Jegger D, Horisberger J, Mucciolo G, von Segesser L K; "A new expandable venous cannula for minimal access heart surgery"; Ann Thorac Surg. 2002 October; 74: S1330-3.
von Segesser L K, Ferrari E, Delay D, Horisberger J, Tozzi P.; "Routine use of self-expanding venous cannulas for cardiopulmonary bypass: Benefits and pitfalls in 100 consecutive cases"; Eur J Cardio-thorac Surg 2008; 34:635-640.
Runge T M, Grover F L, Cohen D J, Bohls F O, Ottmers S E, Saadatmanesh; "Comparison of a steady flow pump to a preload responsive pulsatile pump in left atrial-to-aorta bypass in canines"; Artif Organs. 1991 February; 15(1):35-41.

Although particular embodiments have been disclosed herein in detail, this has been done by way of example for purposes of illustration only, and is not intended to be limiting with respect to the scope of the embodiments of the present disclosure. In particular, it is contemplated that various substitutions, alterations, and modifications may be made without departing from the spirit and scope of any invention disclosed herein, and different features may be assembled with one or another (or others) of the disclosed embodiments, as well as one or more disclosed embodiments may be combined to present further embodiments. Thus, other aspects, advantages, and modifications are considered to be within the scope of the disclosed embodiments.

What is claimed is:

1. A method for vascular draining using a self-expanding cannula, the method comprising:
providing a self-expandable vascular cannula having a length of between about 30 cm and about 70 cm, wherein the cannula includes a low profile conformation for positioning into a blood vessel and a normal profile conformation after positioning, the cannula having an intravascular interior for receiving and draining the entire volume of blood from the blood vessel when the cannula is expanded in the blood vessel;
configuring the cannula for positioning within a blood vessel;
positioning the cannula in the blood vessel;
expanding, subsequent to the positioning within the blood vessel, the cannula to the normal profile conformation such that nearly the entire length of the cannula conforms to the inside wall of the blood vessel; and
applying a driving pressure to the cannula thereby initiating blood draining from the blood vessel via the cannula and draining the entire volume of blood from the blood vessel.

2. The method according to claim 1, wherein the blood vessel is a vein.

3. The method according to claim 2, wherein the method prevents venous collapse.

4. The method according to claim 1, wherein the vascular drainage is performed during drainage for cardio-pulmonary bypass.

5. The method according to claim 1, wherein the cannula is provided in a trans-jugular or trans-subclavian fashion.

6. The method according to claim 1, wherein the cannula is provided in any one of: a trans-femoral, trans-iliac, transjugular, and/or trans-subclavian fashion.

7. The method according to claim 1, wherein multiple cannulas are provided via any one or more of: trans jugular, trans-subclavian, and/or via the groin.

8. The method according to claim 1, wherein the cannula is provided through the right atrium into the inferior vena cava, which reaches beyond the liver to the iliac or femoral vein.

9. The method according to claim 6, wherein the trans-femoral cannulation is performed by passing the cannula through the right atrium into the superior vena cava.

10. The method of claim 9, wherein the cannula passes the subclavian vein.

11. The method of claim 10, wherein the cannula enters the jugular vein.

12. The method according to claim 6, wherein the trans-jugular or trans-subclavian cannulation are performed by passing the cannula through the superior vena cava and the right atrium into the inferior vena cava.

13. The method according to claim 12, wherein the cannula passes the iliac vein.

14. The method according to claim 13, wherein the cannula enters the femoral vein.

15. The method according to claim 1, wherein multiple cannulas are provided, wherein at least one of the cannulas are provided through the right atrium into the superior and the inferior vena cava, and/or directly into both caval veins.

16. The method according to claim 1, wherein the cannula is a self-expanding cannula, and/or include an open wall design.

17. The method according to claim 1, wherein the cannula is a rectilinear cannula with multiple side holes.

18. The method according to claim 1, wherein drainage is enhanced via the use of a diabolo-shape of the cannula.

19. A system for vascular draining via a self-expanding cannula, the system comprising:
- a self-expanding vascular cannula having a length of between about 30 cm and about 70 cm, wherein the cannula includes a low profile conformation and a normal profile conformation, the cannula having an intravascular interior for receiving and draining the entire volume of blood from the blood vessel when the cannula is expanded in the blood vessel;
- positioning means for positioning the cannula within a blood vessel and for expanding, subsequent to positioning of the cannula, the cannula to the normal profile conformation such that nearly the entire length of the cannula conforms to the inside wall of the blood vessel; and
- pressure means for applying a driving pressure to the cannula, wherein the driving pressure initiates draining of blood via the cannula and drains the entire volume of blood in the blood vessel.

20. The system of claim 19, wherein the positioning means is selected from the group consisting of an obturator, a catheter, a mandrel and a sheath.

21. The system of claim 19, wherein the pressuring means comprises a device selected from the group consisting of a centrifugal pump and a vacuum.

22. A system for vascular draining comprising:
- a vascular cannula having a length of between about 30 cm and about 70 cm, wherein the cannula includes a low profile conformation and a normal profile conformation, the cannula having an intravascular interior for receiving and draining the entire volume of blood from the blood vessel when the cannula is expanded in the blood vessel;
- means for changing the conformation of the cannula;
- positioning means for positioning the cannula within a blood vessel and for expanding, subsequent to positioning of the cannula, the cannula to the normal profile conformation such that nearly the entire length of the cannula conforms to the inside wall of the blood vessel; and
- pressure means for applying a driving pressure to the cannula, wherein the driving pressure initiates draining of blood via the cannula and drains the entire volume from blood in the blood vessel.

23. The system of claim 22, wherein the means for changing the conformation of the cannula is selected from the group consisting of: a mandrel, an electric motor, a change in pressurization, a wrapping string, a balloon and a sheath.

\* \* \* \* \*